(12) United States Patent
Sparks et al.

(10) Patent No.: US 7,509,175 B2
(45) Date of Patent: Mar. 24, 2009

(54) METHOD AND DEVICES FOR STIMULATION OF AN ORGAN WITH THE USE OF A TRANSECTIONALLY PLACED GUIDE WIRE

(75) Inventors: Kurt D. Sparks, San Carlos, CA (US); Charles R. Brynelsen, Menlo Park, CA (US); Mir A. Imran, Los Altos Hills, CA (US)

(73) Assignee: Intrapace, Inc., Mountain View, CA (US)

(*) Notice: Subject to any disclaimer, the term of this patent is extended or adjusted under 35 U.S.C. 154(b) by 0 days.

(21) Appl. No.: 11/830,41 9

(22) Filed: Jul. 30, 2007

(65) Prior Publication Data
US 2008/0051850 A1    Feb. 28, 2008

Related U.S. Application Data

(60) Provisional application No. 60/821,370, filed on Aug. 3, 2006.

(51) Int. Cl.
*A61N 1/05* (2006.01)
(52) U.S. Cl. ...................................... 607/133
(58) Field of Classification Search .................. 607/40, 607/133
See application file for complete search history.

(56) References Cited

U.S. PATENT DOCUMENTS

| 3,411,507 A | 11/1968 | Wingrove |
| 3,646,940 A | 3/1972 | Timm et al. |

(Continued)

FOREIGN PATENT DOCUMENTS

EP    0 129 483    2/1984

(Continued)

OTHER PUBLICATIONS

Joshi, Girish P., "Anesthesia for laparoscopic surgery", Canadian Journal of Anesthesia 49:R11 (2002), Jun. 23, 2002.*

(Continued)

*Primary Examiner*—Carl H Layno
*Assistant Examiner*—Yun Haeng Lee
(74) *Attorney, Agent, or Firm*—Townsend and Townsend and Crew LLP

(57) ABSTRACT

Devices, systems and methods are provided for electrical stimulation of a body organ, particularly within the gastrointestinal tract. In preferred embodiments, the stomach is the organ within the gastrointestinal tract which is targeted for such stimulation. A guide wire or other delivery device is positioned within the body so as to transect the stomach wall. Devices and systems are then advanced over the guide wire for attachment to the stomach wall. The guide wire may be placed by endoscopic, open, laparoscopic or a modified percutaneous approach. In a modified percutaneous approach, the stomach is accessed without the use of general anesthesia by advancing a needle through the abdomen, transecting the stomach wall with the needle and advancing the guide wire through the needle. In some embodiments, particularly for use in obese patients, the modified percutaneous approach includes advancing a trocar through the tissue of the patient toward the outer surface of the organ and advancing the needle through the trocar prior to transecting the wall with the needle.

5 Claims, 19 Drawing Sheets

U.S. PATENT DOCUMENTS

| | | |
|---|---|---|
| 3,662,758 A | 5/1972 | Glover |
| 3,677,251 A | 7/1972 | Bowers |
| 3,735,766 A | 5/1973 | Bowers et al. |
| 3,796,221 A | 3/1974 | Hagfors |
| 3,815,611 A | 6/1974 | Denniston, III |
| 3,835,865 A | 9/1974 | Bowers |
| 4,102,344 A | 7/1978 | Conway et al. |
| 4,153,059 A | 5/1979 | Fravel et al. |
| RE30,366 E | 8/1980 | Rasor et al. |
| 4,338,945 A | 7/1982 | Kosugi et al. |
| 4,431,000 A | 2/1984 | Butler et al. |
| 4,571,556 A | 2/1986 | Gnerlich et al. |
| 4,628,928 A | 12/1986 | Lowell |
| 4,690,145 A | 9/1987 | King-Smith et al. |
| 4,699,143 A | 10/1987 | Dufresne et al. |
| 4,823,808 A | 4/1989 | Clegg et al. |
| 4,921,481 A | 5/1990 | Danis et al. |
| 4,925,446 A | 5/1990 | Garay et al. |
| 5,111,816 A | 5/1992 | Pless et al. |
| 5,112,310 A * | 5/1992 | Grobe .................. 604/175 |
| 5,188,104 A | 2/1993 | Wernicke et al. |
| 5,197,491 A | 3/1993 | Anderson et al. |
| 5,217,449 A | 6/1993 | Yuda et al. |
| 5,248,302 A * | 9/1993 | Patrick et al. ............... 604/178 |
| 5,259,399 A * | 11/1993 | Brown .................. 128/897 |
| 5,292,344 A | 3/1994 | Douglas |
| 5,415,181 A | 5/1995 | Hogrefe et al. |
| 5,423,872 A | 6/1995 | Cigaina |
| 5,540,730 A | 7/1996 | Terry, Jr. et al. |
| 5,558,640 A | 9/1996 | Pfeiler et al. |
| 5,690,691 A | 11/1997 | Chen et al. |
| 5,716,392 A | 2/1998 | Bourgeois et al. |
| 5,792,048 A | 8/1998 | Schaefer |
| 5,800,445 A | 9/1998 | Ratcliff et al. |
| 5,836,994 A | 11/1998 | Bourgeois |
| 5,861,014 A | 1/1999 | Familoni |
| 5,928,195 A | 7/1999 | Malamud et al. |
| 5,935,107 A * | 8/1999 | Taylor et al. ........... 604/164.04 |
| 5,993,473 A | 11/1999 | Chan et al. |
| 5,995,872 A | 11/1999 | Bourgeois |
| 6,004,319 A | 12/1999 | Goble et al. |
| 6,026,326 A | 2/2000 | Bardy |
| 6,030,364 A * | 2/2000 | Durgin et al. .......... 604/164.01 |
| 6,041,258 A | 3/2000 | Cigaina et al. |
| 6,083,249 A | 7/2000 | Familoni |
| 6,091,992 A | 7/2000 | Bourgeois et al. |
| 6,097,984 A | 8/2000 | Douglas |
| 6,098,629 A | 8/2000 | Johnson et al. |
| 6,104,955 A | 8/2000 | Bourgeois |
| 6,115,635 A | 9/2000 | Bourgeois |
| 6,205,359 B1 | 3/2001 | Boveja |
| 6,216,039 B1 | 4/2001 | Bourgeois |
| 6,243,607 B1 | 6/2001 | Mintchev et al. |
| 6,285,897 B1 | 9/2001 | Kilcoyne et al. |
| 6,321,124 B1 | 11/2001 | Cigaina |
| 6,327,503 B1 | 12/2001 | Familoni |
| 6,366,814 B1 | 4/2002 | Boveja et al. |
| 6,381,495 B1 | 4/2002 | Jenkins |
| 6,427,089 B1 | 7/2002 | Knowlton |
| 6,449,511 B1 | 9/2002 | Mintchev et al. |
| 6,453,199 B1 | 9/2002 | Kobozev |
| 6,454,785 B2 | 9/2002 | De Hoyos Garza |
| 6,477,423 B1 | 11/2002 | Jenkins |
| 6,510,332 B1 | 1/2003 | Greenstein |
| 6,529,778 B2 | 3/2003 | Prutchi |
| 6,535,764 B2 * | 3/2003 | Imran et al. .................. 607/40 |
| 6,540,789 B1 | 4/2003 | Silverman et al. |
| 6,542,776 B1 | 4/2003 | Gordon et al. |
| 6,564,101 B1 | 5/2003 | Zikria |
| 6,571,127 B1 | 5/2003 | Ben-Haim et al. |
| 6,591,137 B1 | 7/2003 | Fischeli et al. |
| 6,600,953 B2 | 7/2003 | Flesler et al. |
| 6,606,518 B1 | 8/2003 | Cigaina |
| 6,606,523 B1 | 8/2003 | Jenkins |
| 6,609,025 B2 | 8/2003 | Barrett et al. |
| 6,611,715 B1 | 8/2003 | Boveja |
| 6,615,084 B1 | 9/2003 | Cigaina |
| 6,684,104 B2 | 1/2004 | Gordon et al. |
| 6,826,428 B1 | 11/2004 | Chen et al. |
| 6,879,859 B1 | 4/2005 | Boveja |
| 6,895,278 B1 | 5/2005 | Gordon et al. |
| 6,895,279 B2 | 5/2005 | Loeb et al. |
| 7,020,526 B1 | 3/2006 | Zhao |
| 7,054,692 B1 | 5/2006 | Whitehurst et al. |
| 7,120,498 B2 * | 10/2006 | Imran et al. .................. 607/40 |
| 7,255,675 B2 * | 8/2007 | Gertner et al. .................. 600/37 |
| 2002/0055757 A1 * | 5/2002 | Torre et al. .................. 606/192 |
| 2002/0072780 A1 | 6/2002 | Foley |
| 2002/0103424 A1 | 8/2002 | Swoyer et al. |
| 2002/0103521 A1 | 8/2002 | Swoyer et al. |
| 2002/0103522 A1 | 8/2002 | Swoyer et al. |
| 2002/0161414 A1 | 10/2002 | Fiesler et al. |
| 2002/0198570 A1 | 12/2002 | Puskas |
| 2002/0198571 A1 | 12/2002 | Puskas |
| 2003/0055463 A1 | 3/2003 | Gordon et al. |
| 2003/0120328 A1 | 6/2003 | Jenkins et al. |
| 2003/0144708 A1 | 7/2003 | Starkebaum |
| 2003/0195600 A1 | 10/2003 | Tronnes |
| 2003/0212439 A1 | 11/2003 | Schuler et al. |
| 2004/0015201 A1 | 1/2004 | Greenstein |
| 2004/0059393 A1 | 3/2004 | Policker et al. |
| 2004/0088022 A1 | 5/2004 | Chen |
| 2004/0093039 A1 | 5/2004 | Schumert |
| 2004/0133089 A1 | 7/2004 | Kilcoyne et al. |
| 2004/0147816 A1 | 7/2004 | Policker et al. |
| 2004/0162595 A1 | 8/2004 | Foley |
| 2004/0167583 A1 | 8/2004 | Knudson et al. |
| 2004/0172084 A1 | 9/2004 | Knudson et al. |
| 2004/0172085 A1 | 9/2004 | Knudson et al. |
| 2004/0172086 A1 | 9/2004 | Knudson et al. |
| 2004/0172088 A1 | 9/2004 | Knudson et al. |
| 2004/0172095 A1 | 9/2004 | Jenkins et al. |
| 2004/0176812 A1 | 9/2004 | Knudson et al. |
| 2004/0236381 A1 | 11/2004 | Dinsmoor et al. |
| 2004/0236382 A1 | 11/2004 | Dinsmoor et al. |
| 2005/0021101 A1 | 1/2005 | Chen et al. |
| 2005/0038454 A1 | 2/2005 | Loshakove |
| 2005/0049655 A1 | 3/2005 | Boveja et al. |
| 2005/0055039 A1 | 3/2005 | Burnett et al. |
| 2005/0065575 A1 | 3/2005 | Dobak |
| 2005/0089571 A1 | 4/2005 | Berkert et al. |
| 2005/0090873 A1 | 4/2005 | Imran |
| 2005/0096514 A1 | 5/2005 | Starkebaum |
| 2005/0113880 A1 | 5/2005 | Gordon et al. |
| 2005/0131485 A1 | 6/2005 | Knudson et al. |
| 2005/0131486 A1 | 6/2005 | Boveja et al. |
| 2005/0131487 A1 | 6/2005 | Boveja et al. |
| 2005/0137643 A1 | 6/2005 | Mintchev |
| 2005/0137644 A1 | 6/2005 | Boveja et al. |
| 2005/0149141 A1 | 7/2005 | Starkebaum |
| 2005/0149142 A1 | 7/2005 | Starkebaum |
| 2005/0149146 A1 | 7/2005 | Boveja et al. |
| 2005/0159800 A1 | 7/2005 | Marshall et al. |
| 2005/0159801 A1 | 7/2005 | Marshall et al. |
| 2005/0222637 A1 | 10/2005 | Chen |
| 2005/0222638 A1 | 10/2005 | Foley |
| 2005/0251219 A1 | 11/2005 | Evans |
| 2006/0020298 A1 | 1/2006 | Camilleri et al. |
| 2006/0025654 A1 | 2/2006 | Suzuki et al. |
| 2006/0036293 A1 | 2/2006 | Whitehurst et al. |
| 2006/0058851 A1 | 3/2006 | Cigaina |
| 2006/0074335 A1 | 4/2006 | Ben-Oren et al. |
| 2006/0074450 A1 | 4/2006 | Boveja et al. |
| 2006/0074457 A1 | 4/2006 | Imran et al. |

| | | |
|---|---|---|
| 2006/0074458 A1 | 4/2006 | Imran |
| 2006/0085054 A1 | 4/2006 | Zikorus et al. |
| 2006/0089690 A1 | 4/2006 | Gerber |
| 2006/0089699 A1* | 4/2006 | Imran ................. 607/133 |
| 2006/0095078 A1 | 5/2006 | Tronnes |
| 2006/0116736 A1 | 6/2006 | DiLorenzo |
| 2007/0049986 A1 | 3/2007 | Imran |

FOREIGN PATENT DOCUMENTS

| | | |
|---|---|---|
| EP | 0 571 938 | 12/1993 |
| WO | WO 98/43700 | 10/1998 |
| WO | WO 98/53878 | 12/1998 |
| WO | WO 00/30534 | 6/2000 |
| WO | WO 01/58389 | 8/2001 |
| WO | WO 01/76690 | 10/2001 |
| WO | WO 02/26101 | 4/2002 |

OTHER PUBLICATIONS

Bellahsene, et al., Evaluation of a Portable Gastric Stimulator, Ninth Annual Conference of the Engineering in Medicine and Biology Society, 2 pages total. (1987).

Cigaina et al., Gastric Myo-Electrical Pacing As Therapy For Morbid Obesity: Preliminary Results.

Daniel et al., Electrical Activity of the Gastrointestinal Tract as an Indication of Mechanical Activity, Am. J. of Digestive Diseases, 8(1):54-102, (1963).

Eagon et al., Effects of Gastric Pacing on Canine Gastric Motility and Emptying, The American Physiological Society, 265(4):G767-G774, (Oct. 1993).

Eagon et al., Gastrointestinal Pacing, Surgical Clinics of North America, 73(6): 1161-1172 (Dec. 1993).

Electric Stimulation of the Gastrointestinal Tract, GP, p. 151 (Apr. 1964).

Familoni, Efficacy of Electrical Stimulation at Frequencies Higher Than Basal Rate in Canine Stomach, Digestive Diseases and Sciences, 42(5):892-897, (May 1997).

Familoni, et al., Electrical Pacing of the Stomach in Dogs, Engineering in Medicine and Biology Society, IEEE Proceedings of the Annual International Conference, 6:2315-2316 (Oct. 29-Nov. 1, 1992).

Geldof et al., Electrogastrographic Study of Gastric Myoelectrical Activity In Patients With Unexplained Nausea And Vomiting, Gut, 27:799808, (1986).

Hocking, Postoperative Gastroparesis and TachygastriaResponse to Electric Stimulation and Erythromycin, Surgery, 114(3):538-542 (Sep. 1993).

Kelly et al., Role of the Gastric Pacesetter Potential Defined by Electrical Pacing, Canadian J. of Physiology and Pharmacology, 50:1017-1019, (1972).

Kelly, Differential Responses Of The Canine Gastric Corpus And Antrum To Electric Stimulation, Am. J. of Physiology. 226(1):230-234, (Jan. 1974).

Kelly, et al., Pacing The Canine Stomach With Electric Stimulation, Am. J. of Physiology, 222(3):588-594 (Mar. 1972).

Kubota, et al., Manometric Evaluation Of Children With Chronic Constipation Using a Suction-Stimulating Electrode, Eu. J. Pediari. Surg. 2:287-290, (1992).

Miedema et al., Pacing The Human Stomach, Surgery, 143-150, (Feb. 1992).

Sarna et al., Electrical Stimulation of Gastric Electrical Control Activity, Am. 1. of Physiology, 225(1):125-131, (Jul. 1973).

Sarna, et al., Gastric Pacemakers, Gastroenterology. 70:226-231, (1976).

Swain, et al., An Endoscopically Deliverable Tissue-Transfixing Device for Securing Biosensors in The Gastrointestinal Tract, Gastrointestinal Endoscopy, 40(6):730-734 (1994).

* cited by examiner

METHOD AND DEVICES FOR STIMULATION OF AN ORGAN WITH THE USE OF A TRANSECTIONALLY PLACED GUIDE WIRE

CROSS-REFERENCES TO RELATED APPLICATIONS

This application claims priority of U.S. Provisional Patent Application No. 60/821,370 filed on Aug. 3, 2006, incorporated herein by reference for all purposes.

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Electrical stimulation of the gastrointestinal tract has been proposed to treat motility related disorders and other gastrointestinal diseases. The electrical stimulation has been proposed in a number of forms, such as pacing, electrical contractile stimulation or other stimulation, to treat various diseases or symptoms, such as nausea or obesity. Electrical stimulation has also been proposed to treat obesity by altering gastric motility, or by stimulating neural pathways. For example, one treatment method causes the stomach to retain food for a greater duration. Electrical stimulation has also been proposed to slow the gastric emptying to treat a disorder known as dumping syndrome where the stomach empties at an abnormally high rate into the small intestine causing various gastrointestinal disorders.

An early attempt at a gastric stimulation device included an electrode at the end of a nasogastric tube or catheter. The nasogastric tube was passed into the stomach transnasally. Electrical stimulation was applied using an external stimulator unit through the electrode on the end of the tube. The return electrode was placed on the abdomen. This device required a transnasal procedure whenever stimulation was required.

Other devices used to pace the stomach have generally been implanted by accessing the outside of the stomach through an opening in the abdomen, either through open surgery or laparoscopic surgery. For example, electrodes have been attached to the stomach wall with attached leads extending through the abdomen. The leads are connected with a pacemaker device which is implanted in a subcutaneous or sub-muscular pocket at a remote location.

Improved devices, systems and methods of implantation would be desirable for stimulation of the gastrointestinal tract, particularly the stomach. Such devices and systems should be easily implantable, suitable for long term use, safe, and effective in treating the disorder or symptom, to name a few. In particular, such methods should be particularly suitable for treatment of obese patients who may have particular needs and limitations due to their condition. At least some of these objectives will be met by the present invention.

BRIEF SUMMARY OF THE INVENTION

The present invention provides devices, systems and methods for electrical stimulation of a body organ, particularly within the gastrointestinal tract. In preferred embodiments, the stomach is the organ within the gastrointestinal tract which is targeted for such stimulation. Therefore, the stomach will be used for illustrative purposes herein, however it may be appreciated that invention may be used with other organs, hollow organs, tissue layers or elements within the body. The stomach is a hollow organ comprising a stomach wall having an inner surface facing within the organ (i.e. facing the inner lumen of the stomach) and an outer surface facing away from the organ (i.e. facing the peritoneal cavity). The present invention includes a guide wire or other delivery device positioned within the body so as to transect the stomach wall. Thus, the guide wire extends through the outer surface, stomach wall and inner surface, at any angle including perpendicular to the stomach wall. In preferred embodiments, the guide wire extends from the inner surface, through the esophagus and out of the patient's mouth, and/or from the outer surface, through the peritoneal cavity and out of the patient's abdomen. Thus, devices and systems may be delivered through the mouth and/or through the abdomen to the stomach wall for implantation. In some embodiments, a first element of a system of the invention is delivered through the mouth and a second element of the system of the invention is delivered through the abdomen, wherein the first and second elements are part of a system used to stimulate the stomach wall.

In one aspect of the invention, a method is provided for attaching a device to a wall of a hollow organ within a patient, the wall having an inner surface facing within the organ and an outer surface facing away from the organ. In some embodiments, the method comprises positioning a guide wire wherein the guide wire transects the wall of the organ and extends through tissue to an exterior of the patient, and advancing the device over the guide wire from the exterior of the patient toward the organ, wherein the device comprises at least one lead having at least one electrode. The method further comprises attaching the device to the wall of the organ so that the at least one electrode is positioned so as to stimulate the wall.

In some embodiments, positioning the guide wire comprises accessing the organ by a modified percutaneous approach without the use of general anesthesia, wherein the modified percutaneous approach comprises advancing a needle through the tissue of the patient toward the outer surface of the organ, transecting the wall with the needle and advancing the guide wire through the needle. The modified percutaneous approach may further include advancing a trocar through the tissue of the patient toward the outer surface of the organ and advancing the needle through the trocar prior to transecting the wall with the needle. Attaching the device to the wall may comprise positioning the at least one electrode within the wall. Positioning the at least one electrode within the wall may comprise positioning the at least one electrode within or against a muscle layer within the wall. In some embodiments, attaching the device may comprise implanting a pulse generator or stimulator externally of the hollow organ within the patient. Or, attaching the device may comprise attaching the stimulator to the wall of the organ so that the stimulator is implanted within the hollow organ. In such instances, positioning the guide wire may comprise extending the guide wire through a mouth of the patient, the method further comprising advancing the stimulator through the mouth and over the guide wire toward the inner surface of the wall of the hollow organ. Alternatively, attaching the device may comprise implanting the stimulator within the tissue external to the hollow organ.

When the device includes a retention feature, attaching the device to the wall of the organ may comprise positioning the retention feature within the wall of the organ. In some instances, the organ comprises a stomach and the wall includes at least a muscle layer and a submucosal layer. In such instances, positioning the retention feature within the wall of the organ comprises positioning the retention feature between the muscle layer and the submucosal layer. It may be appreciated that when the device includes a fixation feature and a conical segment near the fixation feature, attaching the device to the wall of the organ may comprise positioning the fixation feature against the outer surface of the organ while the conical segment transects the wall.

In another aspect of the present invention, a method of attaching a device having a first portion and a second portion to a wall of a hollow organ within a patient is provided. The wall has an inner surface facing within the organ and an outer surface facing away from the organ. The method includes positioning a guide wire wherein the guide wire transects the wall of the organ, advancing the first portion of the device over the guide wire in a direction toward the inner surface of the wall of the hollow organ, advancing the second portion of the device over the guide wire in an opposite direction toward the outer surface of the wall of the hollow organ, and joining the first and section portions together so as to attach the device to the wall of the hollow organ.

In some embodiments, positioning the guide wire comprises extending the guide wire through a mouth of the patient, and advancing the first portion comprises advancing the first portion through the mouth and over the guide wire toward the inner surface of the wall of the hollow organ. In some instances, positioning the guide wire comprises extending the guide wire through an abdomen of the patient, and advancing the second portion comprises advancing the second portion through the abdomen and over the guide wire toward the outer surface of the wall of the hollow organ. In other instances, positioning the guide wire comprises accessing the organ by a modified percutaneous approach without the use of general anesthesia, wherein the modified percutaneous approach comprises advancing a needle through an abdomen of the patient toward the outer surface of the organ, transecting the wall with the needle and advancing the guide wire through the needle. In some cases, the modified percutaneous approach includes advancing a trocar through the abdomen of the patient toward the outer surface of the organ and advancing the needle through the trocar prior to transecting the wall with the needle.

In yet another aspect of the present invention, a lead is provided for stimulating a wall of a hollow organ within a patient, the wall having an inner surface facing within the organ, an outer surface facing away from the organ and a plurality of layers therebetween. The lead comprises a lead body having a proximal end, a distal end and a guide wire lumen extending through at least a portion of the lead body, the proximal end configured for attachment to a source of electrical energy. The lead also includes a retention feature disposed near the distal end, the retention feature extending radially outwardly from the lead body and configured for positioning between layers of the wall. The lead further includes at least one electrode disposed along the lead so that electrical energy supplied to the at least one electrode stimulates the wall while the retention feature is positioned between layers of the wall.

In some embodiments, when the layers of the wall include a muscle layer and a submucosal layer the retention feature is configured for positioning between the muscle layer and the submucosal layer. It may be appreciated that the at least one electrode may be disposed along the retention feature.

It may also be appreciated that the lead may further comprise a fixation feature disposed proximally of the retention feature, the fixation feature extending radially outwardly from the lead body and configured to contact a surface of the wall. In such instances, the at least one electrode may optionally be disposed along the fixation feature. Or the at least one electrode may be disposed along a segment of the lead body between the retention feature and the fixation feature. In such instances, the at least one electrode may have the shape of a coil, ring, longitudinal strip, or combination of these.

When the layers of the wall include a muscle layer and a submucosal layer, the retention feature and fixation feature may be spaced apart so that the retention feature is positionable between the muscle layer and the submucosal layer while the fixation feature is positionable against a surface of the organ.

In a further aspect of the present invention, a method of attaching a device to a wall of a hollow organ within a patient is provided, the device comprising at least one lead having at least one electrode. The method includes positioning a first guide wire so that the guide wire transects the wall of the organ at a first location, advancing a stimulator over the first guide wire, attaching the stimulator to the wall of the organ at the first location, positioning a second guide wire so that the guide wire transects the wall of the organ at a second location, advancing the at least one lead over the second guide wire, and attaching the at least one lead to the wall of the organ at the second location so that the at least one electrode is positioned so as to stimulate the wall.

When the hollow organ has an outer surface facing tissue extending between the organ and the exterior of the patient, positioning the first guide wire may comprise accessing the organ by a modified percutaneous approach without the use of general anesthesia. In such instances, the modified percutaneous approach may comprise advancing a needle through the tissue of the patient toward the outer surface of the organ, transecting the wall with the needle and advancing the first guide wire through the needle. Likewise, positioning the second guide wire may comprise accessing the organ by a modified percutaneous approach without the use of general anesthesia, wherein the modified percutaneous approach comprises advancing a needle through the tissue of the patient toward the outer surface of the organ, transecting the wall with the needle and advancing the second guide wire through the needle.

DETAILED DESCRIPTION OF THE INVENTION

Figure 1:
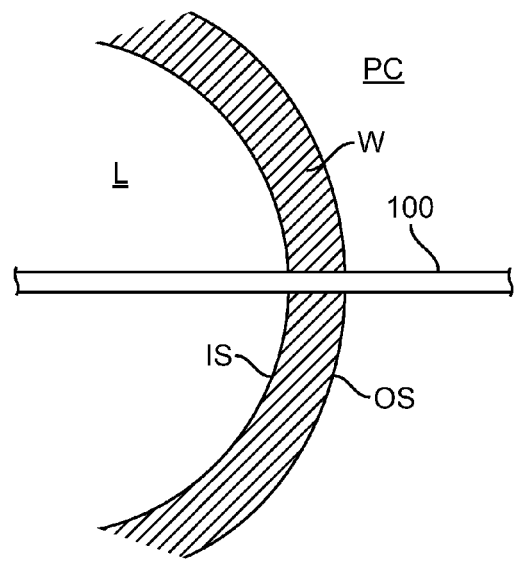
FIG. 1 illustrates a guide wire or other delivery device transectionally positioned across a stomach wall.

Referring to FIG. 1, a guide wire 100 or other delivery device is positioned within a body so as to transect a stomach wall W. The stomach is a hollow organ comprising a stomach wall W having an inner surface IS facing an inner lumen L of the stomach and an outer surface OS facing a peritoneal cavity PC. Thus, the guide wire 100 extends through the outer surface OS, stomach wall W and inner surface IS, at any angle including perpendicular to the stomach wall W.

Figure 2:
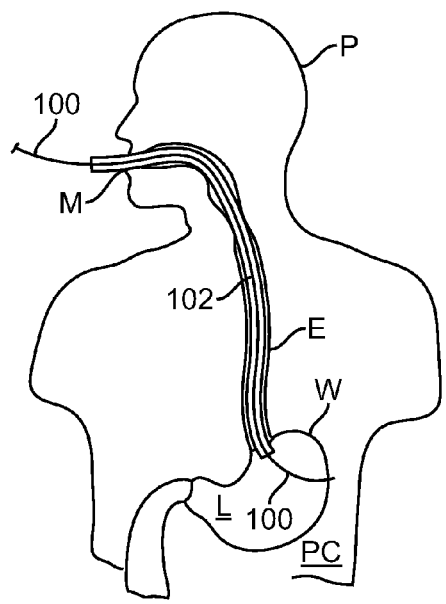
FIG. 2 illustrates positioning of a guide wire such as achieved with an endoscopic approach.

In some embodiments, as illustrated in FIG. 2, the guide wire 100 continues extending through the esophagus E of the patient P and out of the patient's mouth M. This positioning of the guide wire 100 is typically achieved with an endoscopic approach. In this approach, an endoscopic delivery system 102 may be used for delivering a stimulation device or system through the esophagus E and into the stomach lumen L where it is attached to the stomach wall W. In some instances, the endoscopic delivery system 102 includes a flexible endoscope or endoscopic instrument, for locating a preferred site in the stomach for device attachment. The endoscope typically includes one or more conduits through which tools for attaching the stimulation device or system are inserted. Exemplary embodiments of such endoscopic delivery systems 102 and endoscopically delivered stimulation devices and systems are described in U.S. Pat. No. 6,535,764, incorporated herein by reference for all purposes.

Figure 3:
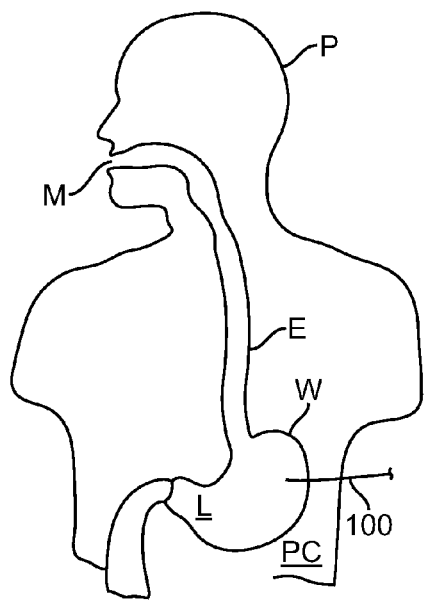
FIG. 3 illustrates positioning of a guide wire such as achieved with an open, laparoscopic or modified percutaneous approach.

In other embodiments, as illustrated in FIG. 3, the guide wire 100 continues extending through a peritoneal cavity PC of a patient P and out of the patient's abdomen. Thus, the guide wire 100 passes between any visceral organs within the peritoneal cavity, through the peritoneum, the muscle layers and associated fascia, subcutaneous fat and all of the layers of the patient's skin to the outside of the body. This positioning of the guide wire 100 is typically achieved with an open or laparoscopic approach. Exemplary embodiments of stimulation devices and systems deliverable with an open or laparoscopic approach and example methodologies are described in U.S. patent application Ser. No. 11/249,661, incorporated herein by reference for all purposes. Typically, the stomach is punctured at a desired lead deployment site with a hollow needle from the outside of the stomach into the stomach. Access to the stomach is achieved by laparoscopy or by an open surgical procedure. A guide wire is positioned through the needle and into the stomach. The needle is then removed leaving the guide wire in place extending through the abdomen into the stomach at the lead deployment site. A lead is then pushed over the guide wire and attached to the stomach wall.

For some patients, an open or laparoscopic approach is less desirable or contraindicated due to, for example, increased risk of complications. Both open and laparoscopic surgery require general anesthesia. In laparoscopy, the patient's peritoneal cavity is inflated with $CO_2$ or another inert inflammable gas, thereby transforming the peritoneal cavity from a virtual to a real cavity. Such inflation raises the diaphragm of the patient upwards, making breathing difficult. Therefore, the patient is placed under general anesthesia and breathing is controlled accordingly. Multiple trocars are then inserted into the gas-filled abdominal cavity so that a video camera and other surgical instruments can be introduced into the abdomen. The operation then proceeds by viewing the video images transmitted by the camera. Generally, a first trocar provides access to the abdomen by the video camera in order to monitor the surgical procedure. A clamp is normally inserted in the second trocar to move or retain portions of the stomach or other viscera depending on the type of operation to be performed. A third trocar provides access for a maneuvering clamp or laparoscopic forceps. A fourth trocar is used for the introduction of instruments to perform the procedure. The procedural complexity and clinical complications associated with placing an obese patient under general anesthesia and positioning a plurality of trocars may contraindicate these patients from these surgical procedures.

Figure 4A:
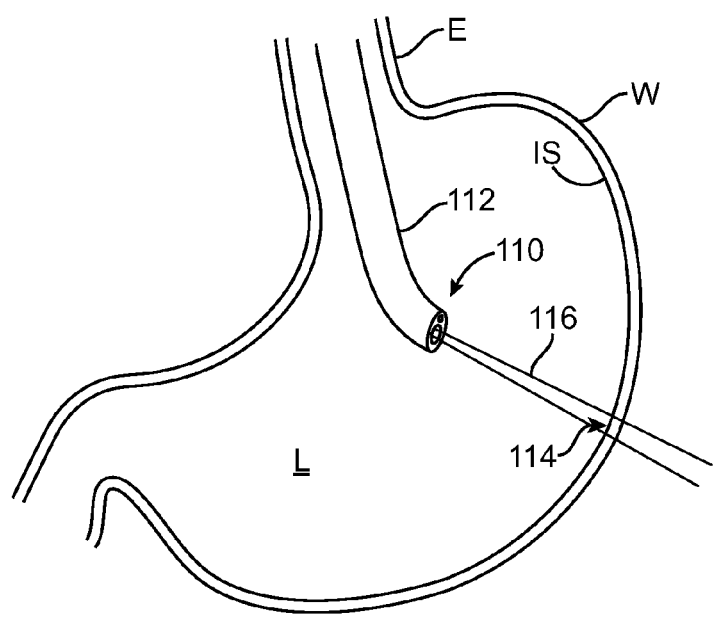
FIGS. 4A-4F illustrate an embodiment of a modified percutaneous approach.

Therefore, positioning of the guide wire 100 as in FIG. 3 may be achieved with a modified percutaneous approach. An embodiment of such a modified percutaneous approach is illustrated in FIGS. 4A-4F. Referring to FIG. 4A, a distal end 110 of an endoscope 112 is advanced through the esophagus E and into the stomach lumen L. In preferred embodiments, the endoscope 112 includes at least optical elements for visualization through its distal end 110, a lumen therethrough for use in insufflating the stomach lumen L, and an illumination mechanism. The stomach lumen L is insufflated to a desired degree to allow viewing of the inner surface IS or mucosal surface of the stomach wall W. A site on the inner surface IS is identified as a target implant site 114 for the placement of a portion of a stimulation device or system, such as a stimulating lead electrode or anchor. Such identification may be achieved by visualization of the inner surface IS with the use of the optical element. Alternatively or in addition, such identification may be achieved by determining a desired pathway through at least a portion of the abdomen. A desired pathway typically minimizes the distance between the patient's skin and the stomach lumen L and reduces the chance of encountering visceral organs as the pathway is developed. To achieve this, light 116 is projected from the endoscope 112 with the use of the illumination mechanism to illuminate the desired target implant site 114, and adjacent portion of the abdomen.

Figure 4B:
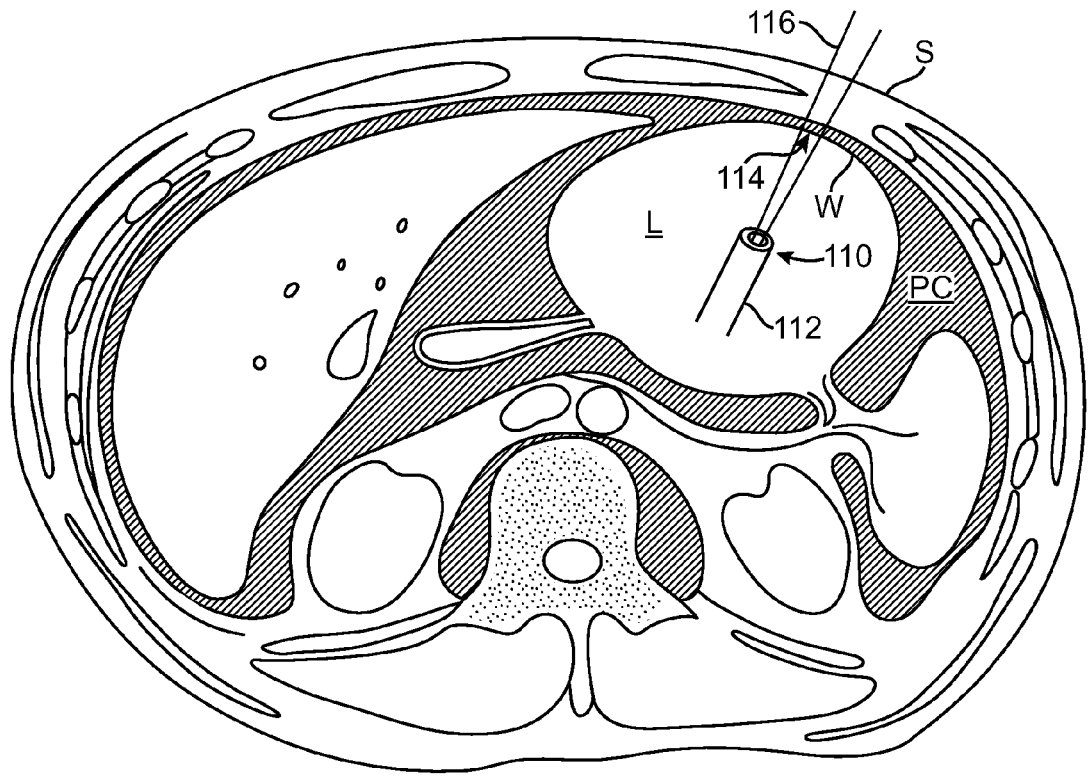

FIG. 4B illustrates a cross-sectional view of the stomach of FIG. 4A within the patient's abdomen. The distal end 110 of the endoscope 112 is shown extending into the stomach lumen L wherein the light 114 trans-illuminates the stomach wall W and the tissues between the wall W and the patient's skin S. Thus, an illuminated area may be seen on the surface of the patient's skin S where the light 114 transects the abdomen. Typically, this pathway is located through an anterior wall of the stomach. The stomach's anterior wall is often closest to the patient's skin (as opposed to the posterior wall) and thus will provide a relatively short and safe pathway from an entry point on the skin to the stomach lumen, with less chance of encountering visceral organs. The target implantation site is also preferably located proximal to the circumferential band of muscle tissue wherein the physical slow wave is initiated in the stomach. This portion of the stomach is generally referred to as the body or fundus-body junction of the stomach. It may be appreciated that alternative or adjunctive methods may be employed to identify desired implantation sites. These methods may include forward-looking ultrasound (phased array, such as manufactured by Volcano Therapeutics), side-looking ultrasound (rotational, such as manufactured by Boston Scientific), magnetic resonance interference (MRI), computer aided tomography (CAT) scan, optical coherence tomography (OCT) or optical coherence reflectometry (OCR), to name a few.

Figure 4C:
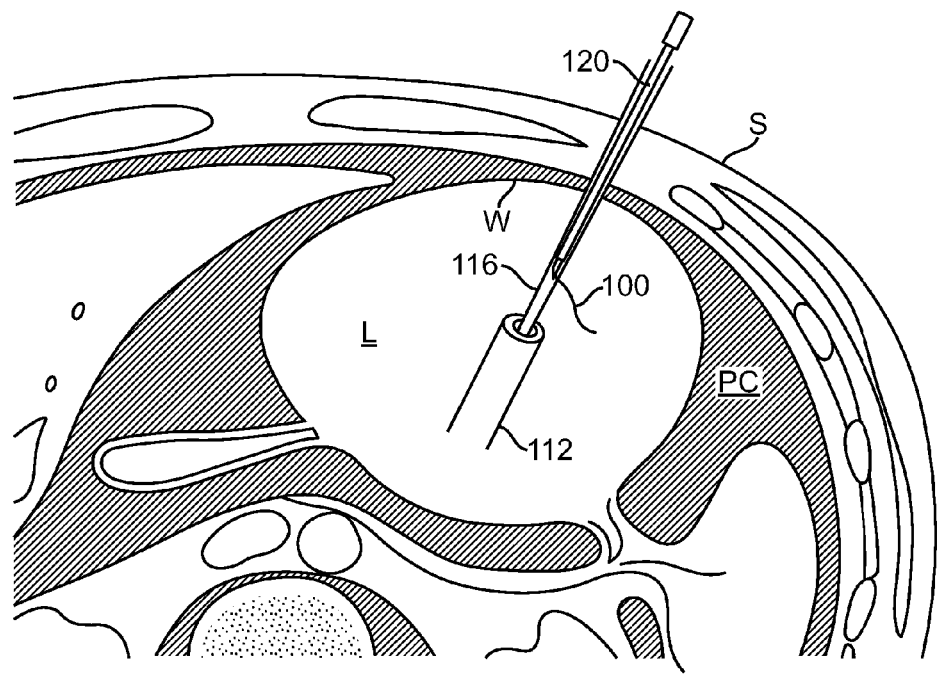
Figure 4D:
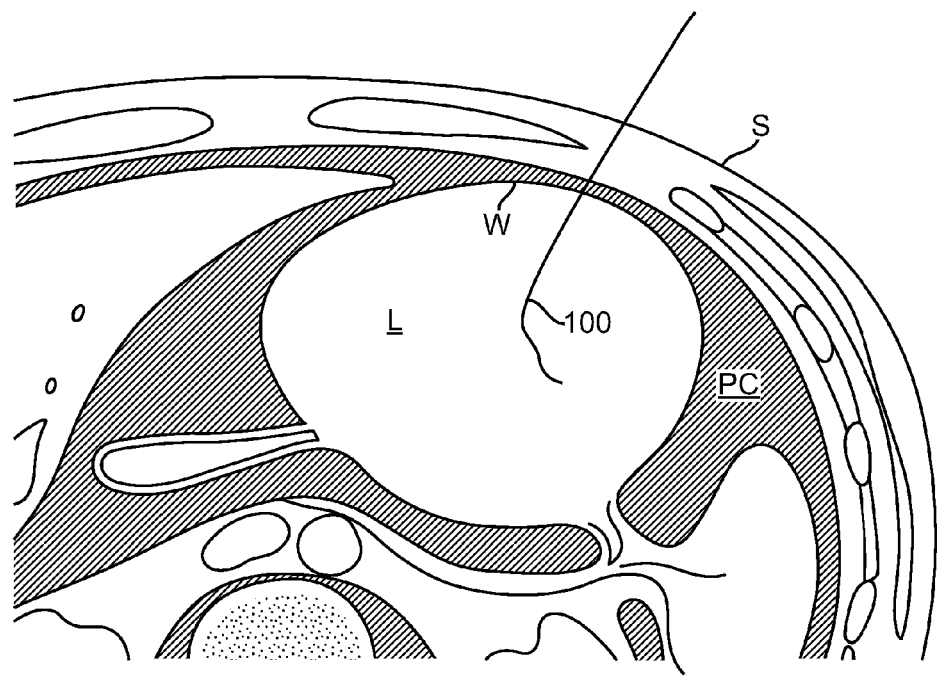

After identifying the desired target implantation site 114, illumination of the site 114 is maintained by the endoscope 112. If the transdermal light 116 is visible on the skin S of the patient's abdomen, its source location at the inner surface IS of the stomach wall W can be estimated with reasonable accuracy. Local injections of anesthetic are administered along the path of the transdermal illumination 116. As shown in FIG. 4C, a needle 120 is then inserted through the patient's skin S and advanced along the path of the illumination 116, transecting the stomach wall W and entering the stomach lumen L. Any suitable needle 120 may be used, including a percutaneous esophageal gastrotomy (PEG) needle. With the tip of the needle 120 positioned within the stomach lumen L, a guide wire 100 is advanced through the needle 120 and into the stomach lumen L. The needle 120 is then fully retracted, leaving the guide wire 100 in place, as illustrated in FIG. 4D.

Figure 4E:
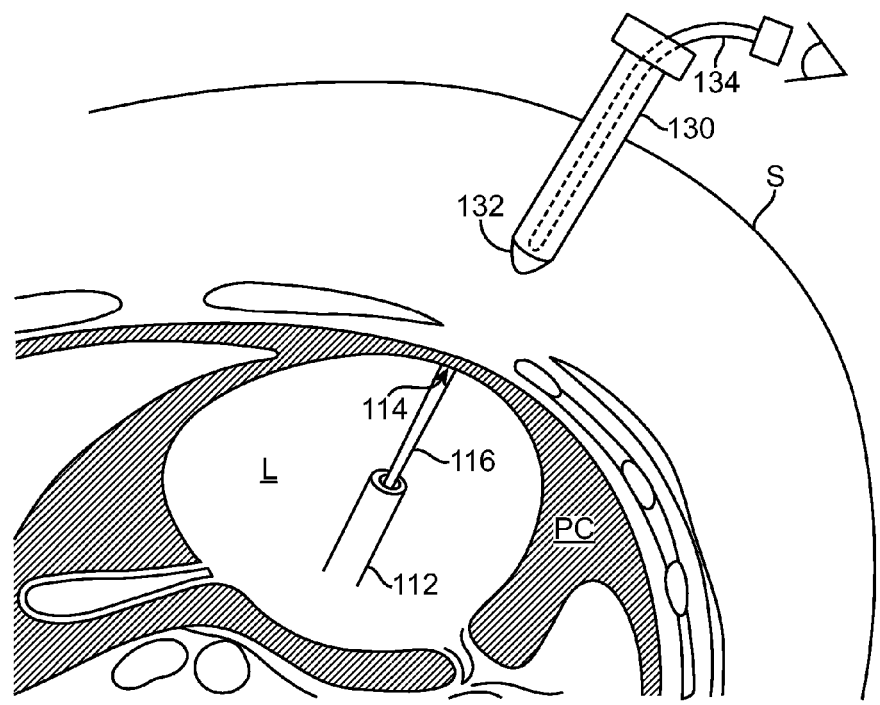
Figure 4F:
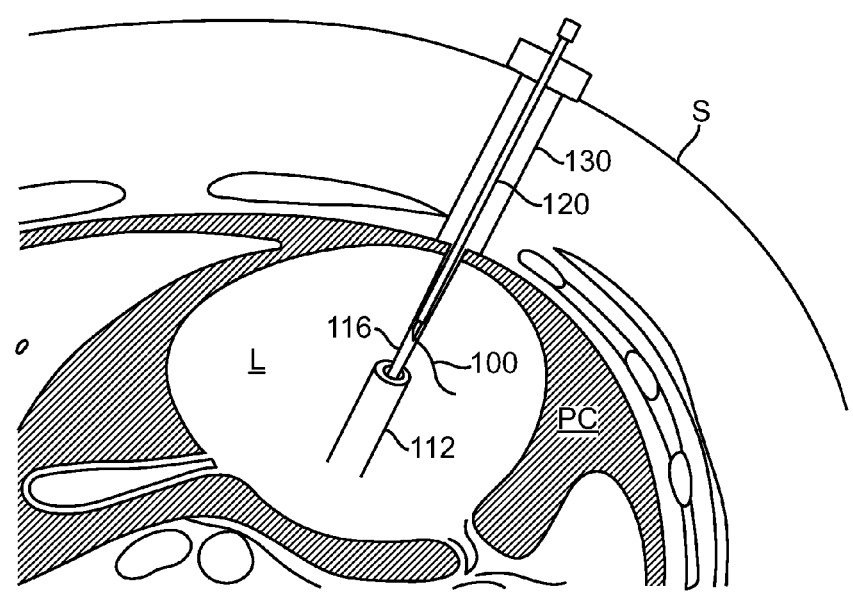

In some patients, particularly obese patients, the transdermal light 116 is not readily visible on the skin S of the patient's abdomen. In obese patients, this may be due to excessive layers of subcutaneous fat. Or, in some instances the light 116 may be at least partially blocked by the spleen, small bowel or liver tissue. When the light 116 is not readily visible, the pathway is created with the use of a trocar 130, as illustrated in FIGS. 4E-4F. Local injections of anesthetic are administered along a projected pathway to the stomach lumen L. A small incision is made in the patient's skin S and a trocar 130 having an atraumatic tip 132 (such as Xcel EndoTip, as manufactured by Ethicon Endovascular) is inserted through the incision, as illustrated in FIG. 4E. The trocar 130 is advanced through the tissues of the abdomen using conventional blunt dissection techniques, taking care not to damage surrounding organs, such as the liver, spleen or small bowel. Visual guidance may be facilitated by the introduction of a laparoscope 134 positioned within the trocar 130. As the stomach wall W is approached, the transdermal light 116 will become visible. Once the tip 132 of the trocar 130 has been advanced to desired implantation site 114 at the stomach wall W, a needle 120 is advanced through the trocar 130, transecting the stomach wall W and entering the stomach lumen L, as illustrated in FIG. 4F. A guide wire 100 is advanced, as shown, through the needle 120 so as to enter the stomach lumen L. Once the guide wire 100 is in place, the trocar 130 and needle 120 may be removed.

In either case, the guide wire 100 need only be advanced into the stomach lumen L a sufficient distance to maintain position of the guide wire 100 without risk of dislodgement when the needle 120 and optionally trocar 130 are removed. In some embodiments, approximately 10 inches of guide wire 100 are advanced into the stomach lumen L, however any suitable amount may be advanced. Likewise, the guide wire 100 may have any suitable diameter. In some embodiments, a standard 0.035" diameter guide wire used for percutaneous transluminal angioplasty (PTA) procedures is used.

Once the guide wire 100 has been placed transecting the stomach wall W, the pathway along the guide wire 100 may be dilated to allow the delivery of devices or systems. Dilation may be achieved with the use of a series of dilators which are advanceable over the guide wire 100. The devices or systems used in gastric stimulation may then be delivered to the stomach wall W through the abdomen.

Figure 5A:
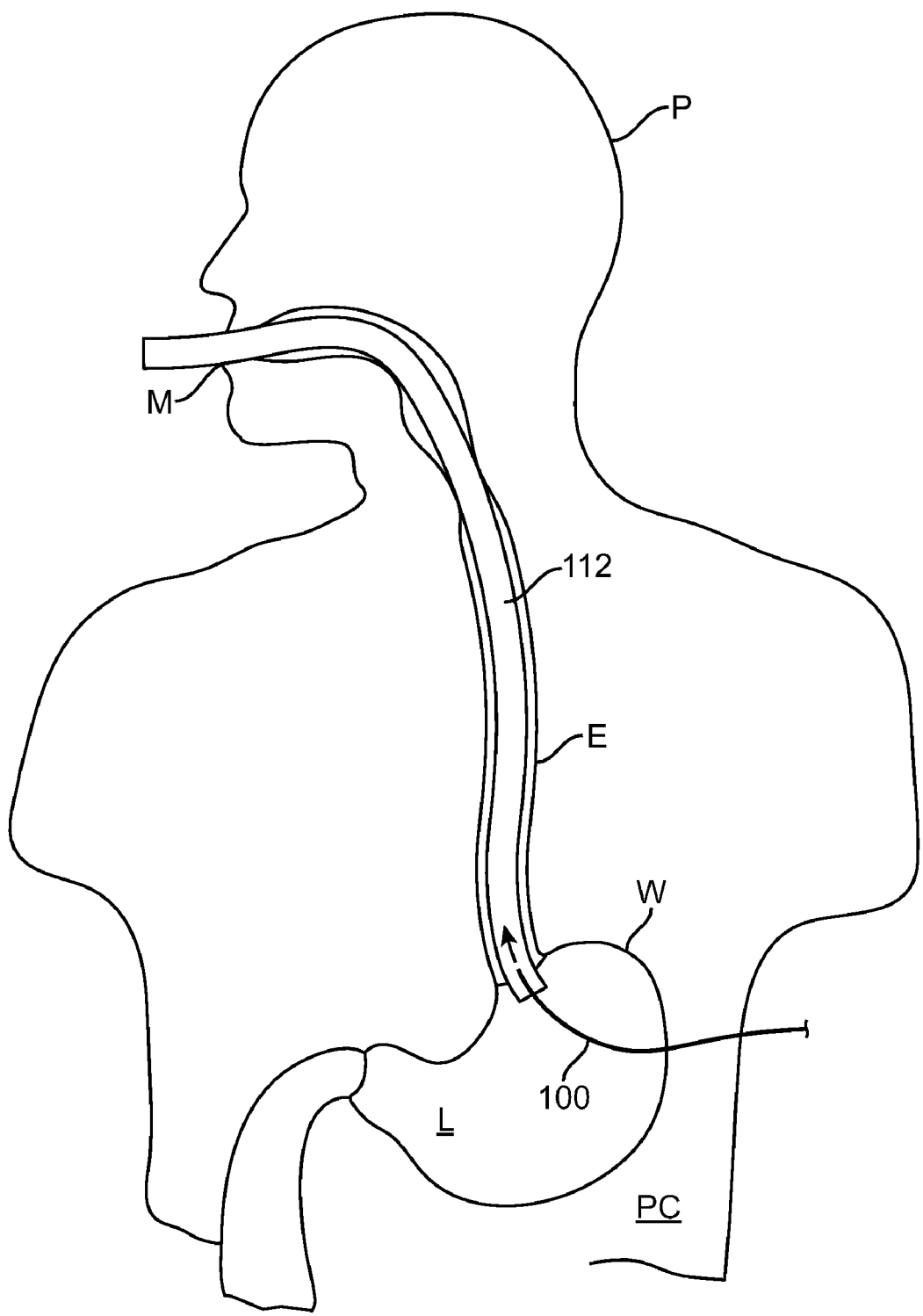
FIGS. 5A-5B illustrate a guide wire positioned to extend from a patient's abdomen, through the stomach wall, and out of the patient's mouth.
Figure 5B:
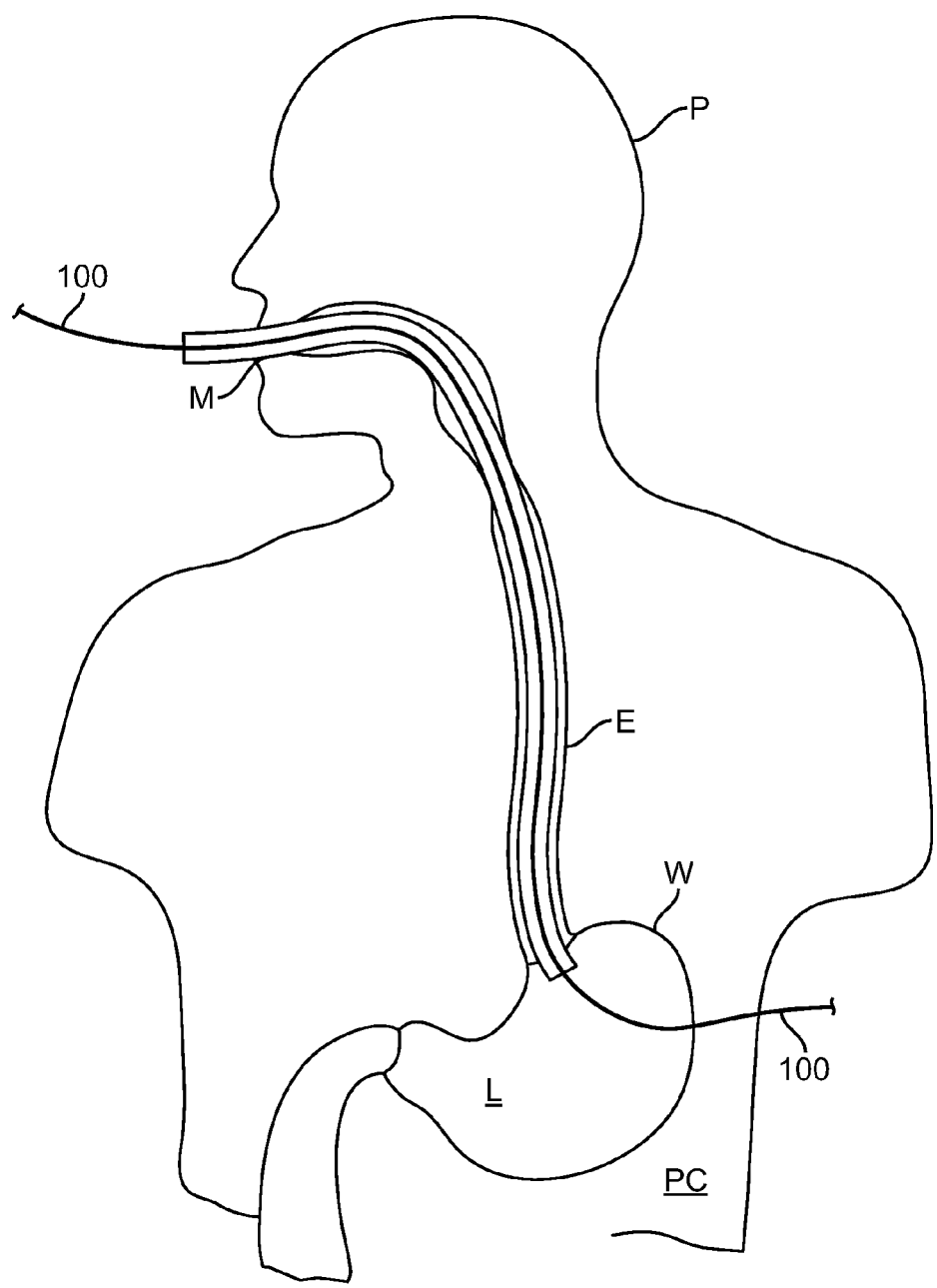

In some embodiments, as illustrated in FIGS. 5A-5B, the guide wire 100 is positioned to extend from the patient's abdomen, through the peritoneal cavity PC, through the stomach wall W, up the esophagus E and out of the patient's mouth. Thus, a continuous pathway is formed through the patient's body, with direct access to both the inner surface and outer surface of the stomach wall from outside of the body. Devices and systems may then be delivered over the guide wire 100, through the mouth and/or through the abdomen to the stomach wall for implantation. In some embodiments, a first element of a system is delivered through the mouth and a second element of the system is delivered through the abdomen, wherein the first and second elements are used in conjunction to stimulate the stomach wall.

To achieve placement of the guide wire 100 along a continuous pathway, the guide wire 100 is first positioned as illustrated in FIG. 3 by an open, laparoscopic or modified percutaneous approach. The distal end of the guide wire 100 is advanced in a retrograde fashion through the patient's lower esophageal sphincter (LES), through the esophagus E and exits the mouth M. Typically, an endoscope 112 is positioned within the esophagus E so that the distal end of the guide wire 100 is advanced up a working channel of the endoscope 1 12. Thus, the distal end of the guide wire 100 exits a proximal entry port of the endoscope's working channel and extends from the mouth M. The endoscope 112 is then removed, leaving the guide wire 100 in place. Alternatively, a tube having a lumen may be positioned along side the endoscope 112 wherein the distal end of the guide wire 100 is advanced in a retrograde fashion within the lumen of the tube exiting the mouth M. The tube may then be removed, leaving the guide wire 100 in place and maintaining the endoscope 112 in position within the stomach lumen L. Typically, a guide wire length of at least approximately 300 cm is sufficient to place the guide wire 100 as in FIG. 5B, however any suitable length may be used.

Figure 6:
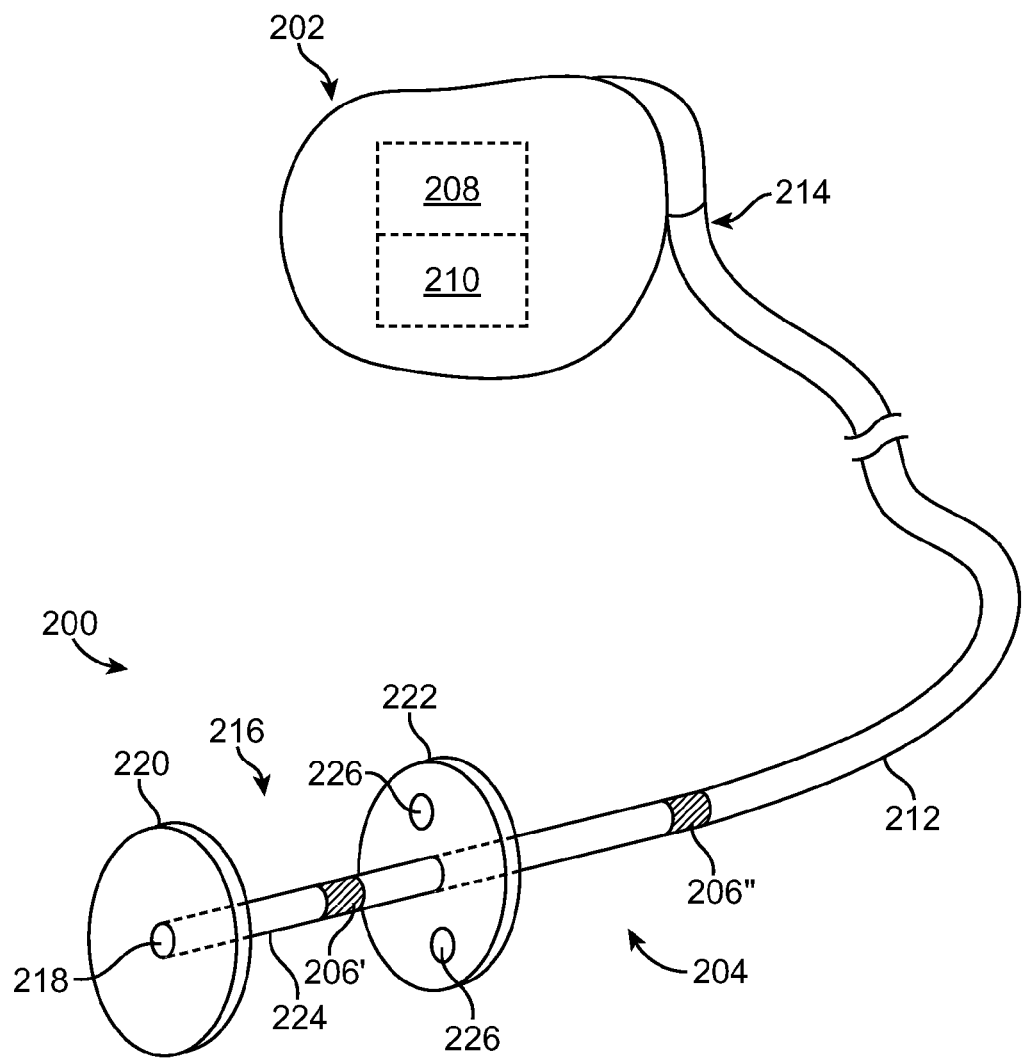
FIG. 6 illustrates an embodiment of a device which may be advanced over a transectionally placed guide wire for use in stimulating the stomach wall.

Once the guide wire 100 is in place transecting the stomach wall W, as in FIG. 2, FIG. 3 or FIG. 5B, devices or systems may be advanced over the guide wire 100 for use in stimulating the stomach wall W. An example of such a device 200 is illustrated in FIG. 6. In this embodiment, the device 200 comprises a pulse generator or stimulator 202 and an electrically conductive lead 204 having at least one electrode 206. The stimulator 202 comprises electronics 208 and a power source 210 which are coupled to the lead 204 so as to provide electrical energy to the at least one electrode 206. The lead 204 is configured to apply energy to the stomach wall W via the at least one electrode 206 and the stimulator 202 is configured to be implanted at a suitable location.

In this embodiment, the lead 204 comprises a flexible lead body 212 having a proximal end 214 which is connectable with the stimulator 202 and a distal end 216. The flexible lead body 212 may be comprised of any suitable material, particularly thermoset plastics such as silicone, fluorosilicone, synthetic rubber and fluoropolymer elastomers such as Viton® (DuPont Performance Elastomers), perfluoroelastomers such as Kalrez® ((DuPont Performance Elastomers), other polymers within these families, other polymers, or any combination of these, to name a few. The flexible lead body 212 also includes a guide wire lumen 218 extending at least through the distal end 216 which is used for advancing the lead 204 over the guide wire 100. In this embodiment, the lead 204 also includes a retention feature 220 and a fixation feature 222 disposed near the distal end 216. Both features 220, 222 extend radially outwardly from the lead body 212 and are spaced apart by a segment 224. The segment 224 may be comprised of any suitable material, including polymers, stainless steel, alloys, quaternary alloys such as MP35N having a nominal composition of Nickel 35%, Cobalt 35%, Chromium 20%, Molybdenum 10%, nylons, Pebax, polyetheretherketone (PEEK) or any combination of these, to name a few. In FIG. 6, the features 220, 222 are illustrated as circular or disc-shaped, however the features 220, 222 may have any suitable shape including oval, square, triangle, rectangle, crescent, polygon, etc. The features 220, 222 are flexible so as to flex into a collapsed, folded, or conical configuration for delivery through a sheath or delivery catheter as the lead 204 is advanced over the guide wire 100. The features 220, 222 may be comprised of any suitable material, including thermoset plastics such as silicone, fluorosilicone, synthetic rubber and fluoropolymer elastomers such as Viton® (DuPont Performance Elastomers), perfluoroelastomers such as Kalrez® ((DuPont Performance Elastomers), other polymers within these families, other polymers, or any combination of these, to name a few. In preferred embodiments, the features 220, 222 are comprised of a low durometer silicone having a hardness 50 Shore A. In addition, the lead 204 may be partly or entirely fabricated by injection molding or transfer molding. In some embodiments, this allows the features 220, 222, segment 224 and lead body 212 to be formed as a single unit.

Figure 7A:
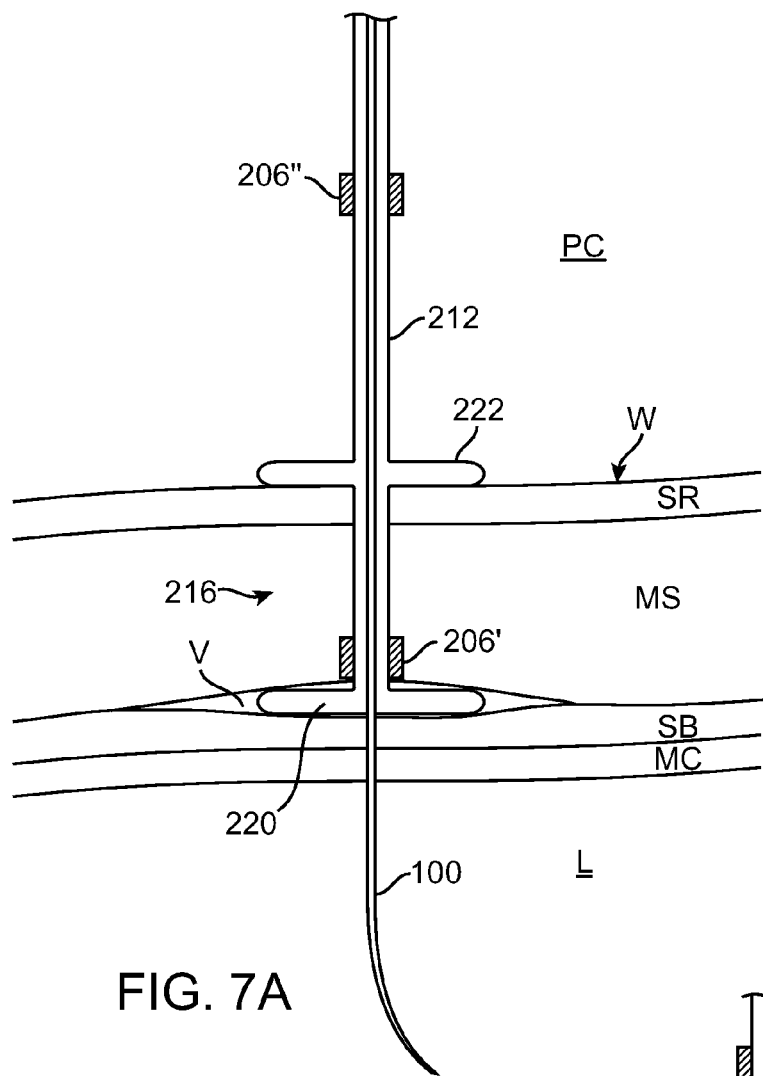
FIGS. 7A-7B provides cross-sectional illustrations of the device of FIG. 6 engaging the stomach wall.
Figure 7B:
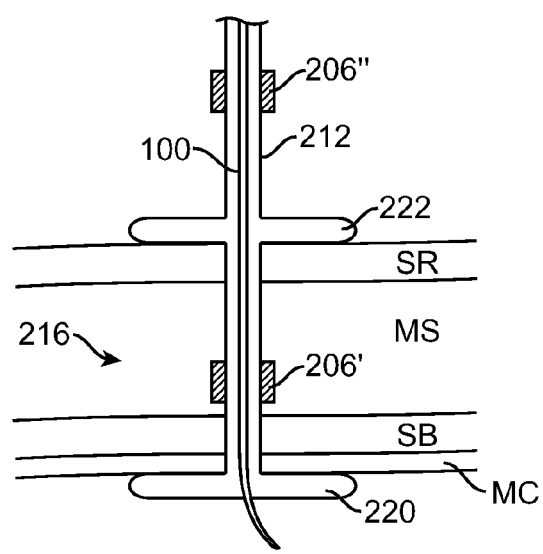

FIGS. 7A-7B illustrate the device 200 of FIG. 6 advanced over a transectionally placed guide wire 100 which has been placed such as by an open, laparoscopic or modified percutaneous approach. In this embodiment, the device 200 is advanced from outside the patient's abdomen, through the peritoneal cavity PC to the stomach wall W. The stomach wall W includes a serosal layer SR, a muscle layer MS, a submucosal layer SB, and a mucosal layer MC. Referring to FIG. 7A, as the device 200 is advanced, the retention feature 220 crosses the serosal layer SR and muscle layer MS until reaching a virtual space V between the muscle layer MS and the submucosal layer SB. The virtual space V is evidenced by the ability of the muscle layer MS and submucosal layer SB to easily slide against each other within a localized area. This characteristic may be exploited to facilitate the placement of the retention feature 220 therein by endoscopically injecting saline into this interface, producing a local saline "bubble" and locally separating the muscle layer MS from the submucosal layer SB. The retention feature 220 is positioned within the virtual space V, between the muscle layer MS and the submucosal layer SB, as shown. The saline bubble may then be aspirated. Such positioning automatically places the fixation feature 222 near the outer surface OS of the stomach wall W and assists in securing the distal end 216 of the lead 204 to the stomach wall W. This in turn holds the electrodes 206' in contact with the muscularis layer MS (allowing stimulation of full cross-section of muscularis layer MS) and optionally provides an additional surface upon which to mount electrodes. In addition, the retention feature 220 resists pull out of the distal end 216. Thus, the retention feature 220 may be used instead of suturing the fixation feature 222 in place to secure the distal end 216 of the lead 204, or the retention feature 220 may be used to stabilize the lead 204 while the fixation feature 222 is sutured in place Alternatively, the retention feature 220 may be positioned against the inner surface IS of the stomach wall W, as illustrated in FIG. 7B,or between or within any layers of the stomach wall W.

Upon delivery, the retention feature 220 resumes its thermoset expanded shape, allowing the feature 220 to desirably seat and maintain position between the layers MS, SB while remaining flexible so as to contour to the stomach wall W as the stomach wall W moves. In this embodiment, the retention feature 220 has a diameter in the range of approximately 0.25 inches to 1 inch, and a thickness in the range of approximately 0.005 to 0.040 inches, however other sizes and thicknesses may be used. Further, in this embodiment, the retention feature 220 is comprised of a polymer having a durometer in the range of approximately 30 Shore A to 70 Shore A, but other durometers may be used. In some embodiments, as the durometer of the polymer is increased, both the diameter and the wall thickness of the retention feature 220 is decreased to provide a balance of physical characteristics in support of lead deployment, chronic healing and implant stability.

Referring again to FIG. 7, the fixation feature 222 is shown positioned against the outer surface OS of the stomach wall W. The fixation feature 222 may have any of the aspects of the retention feature 220, such as size, shape, thickness, durometer, etc. In addition, the fixation feature 222 may include suturing or clipping holes 226 for suturing or clipping the fixation feature 222 to the outer surface OS or serosal layer SR of the stomach wall W to provide acute positional stability to the distal end 216 of the lead 204. Desired positioning of the distal end 216 of the lead 204 is collectively supported by the retention feature 220 and the fixation feature 222, wherein portions of the stomach wall W are disposed therebetween. The retention feature 220 and fixation feature 222 may be spaced any suitable distance apart, such as approximately 2 mm-1 cm apart, preferably 2 mm-12 mm apart, more preferably 4 mm-10 mm apart.

As healing occurs after implantation, a fibrous capsule typically forms around the distal end 216 of the lead 204. This may cause the retention feature 220 to become more securely embedded within the stomach wall W. Alternatively or in addition, the healing response may also form a fibrous pocket of tissue to encapsulate the fixation feature 222, causing the fixation feature 222 to become securely attached to the outer surface OS of the stomach wall W.

Referring back to FIG. 6, one or more electrodes 206 are located on the lead 204. The electrodes 206 may be comprised of any suitable material, such as platinum or platinum-iridium (such as manufactured by Johnson-Mathey, Wayne, Pa.), or non-iron-containing metals, such as alloys or quaternary alloys such as MP35N having a nominal composition of Nickel 35%, Cobalt 35%, Chromium 20%, Molybdenum 10%, (such as manufactured by Fort Wayne Metals, Fort Wayne, Ind.). The one or more electrodes 206 are connected with the stimulator 202, particularly the electronics 208 and power source 210, by at least one electrical conductor. The electrical conductors may be comprised of any suitable material, including stainless steel, platinum-iridium, alloys, quaternary alloys such as MP35N, or metals, to name a few. In some embodiments, the at least one electrical conductor comprises a multi-stranded cable. For example, the multi-stranded cable may include 7 bundles, wherein each bundle includes 19 strands. Each strand may have a diameter of, for example, approximately 0.0012". A cable configuration of this type may have a nominal diameter of approximately 0.018". Many other configurations may be applicable, for example, with strand diameters ranging from approximately 0.0012" to 0.002" and cable diameters ranging from approximately 0.010" to 0.020".

Figure 8:
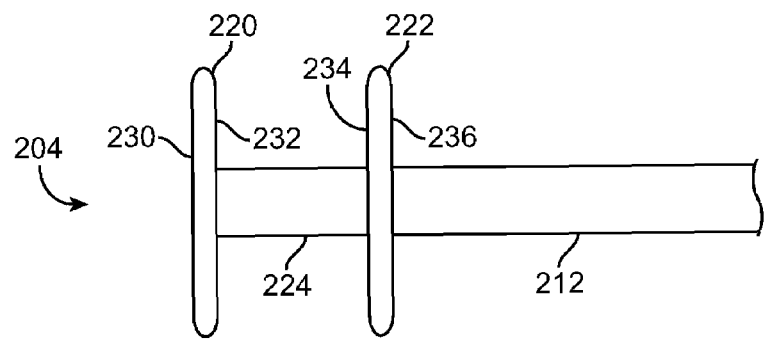
FIG. 8 provides a side view of the device of FIG. 6.
Figure 9A:
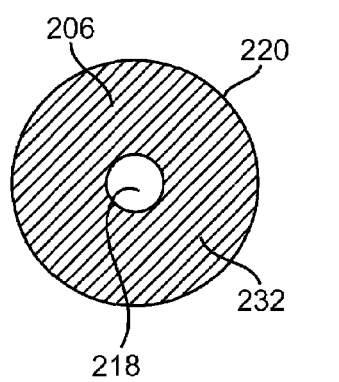
FIGS. 9A-9C, 10, 11 illustrate example electrodes on the device of FIG. 6.
Figure 9B:
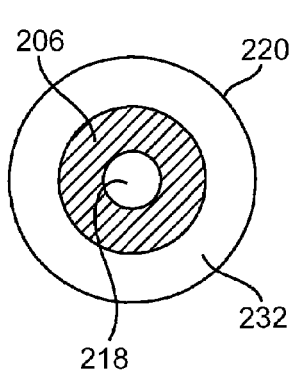
Figure 9C:
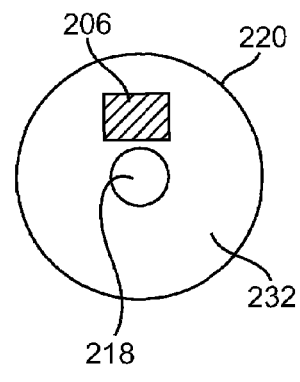

As shown in FIG. 6, a first electrode 206' is located on the segment 224 between the retention feature 220 and fixation feature 222, and a second electrode 206" is located along the lead 204 proximal to the fixation feature 222. However, it may be appreciated that the one or more electrodes 206 may be disposed on a variety of surfaces along the lead 204. For example, referring to FIG. 8, electrodes 206 may be disposed along a distal surface 230 of the retention feature 220, a proximal surface 232 of the retention feature 220, along the segment 224 between the retention feature 220 and fixation feature 222, along a distal surface 234 of the fixation feature 222, along a proximal surface 236 of the fixation feature 222, and/or along the lead body 212 proximal to the fixation feature 222. FIGS. 9A-9C illustrate example embodiments of an electrode 206 disposed along the proximal surface 232 of the retention feature 220. FIG. 9A illustrates the electrode 206 substantially covering the proximal surface 232, surrounding the guide wire lumen 218. FIG. 9B illustrates the electrode 206 having a circular shape surrounding the guide wire lumen 218, wherein the diameter of the electrode is less than the diameter of the retention feature 220. FIG. 9C illustrates the electrode 206 having a square shape offset from the guide wire lumen 218. It may be appreciated that any number of electrodes 206 may be present along the surface 232, and these electrodes 206 may have any shape, size or arrangement. Further, it may be appreciated these examples and description are also applicable to electrodes disposed along the distal surface 230 of the retention feature 220, the distal surface 234 of the fixation feature 222, and the proximal surface 236 of the fixation feature 222.

Figure 10:
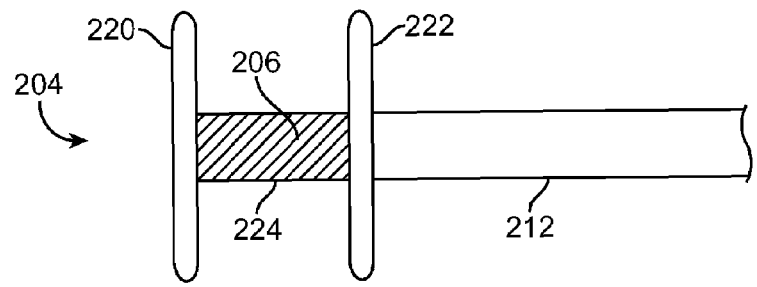
Figure 11:
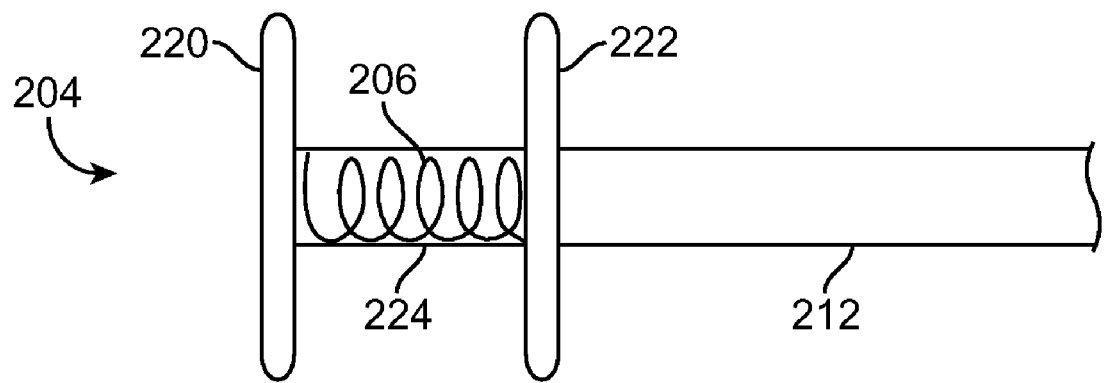

As mentioned, one or more electrodes 206 may be disposed along the segment 224 between the retention feature 220 and the fixation feature 222. FIG. 10 illustrates an electrode 206 substantially covering the segment 224. It may be appreciated that the electrode 206 may cover a portion or the entire circumference of the segment 224 along any length of the segment 224. For example, the electrode 206 may comprise a circumferential ring extending around a portion of the segment 224 or the electrode 206 may comprise a longitudinal strip extending along a portion of the segment 224. The longitudinal strip shape increases contact surface area along the transecting pathway through the stomach wall W, particularly providing more points of contact along the transecting pathway. And, when the longitudinal strip acts as a stimulating electrode, the longitudinal strip shape assists in providing a distributed density of stimulation energy along the transecting pathway. It may be appreciated that any number of electrodes 206 may be present along the segment 224, and these electrodes 206 may have any shape, size or arrangement. For example, FIG. 11 illustrates the electrode 206 having a coil shape.

Figure 12:
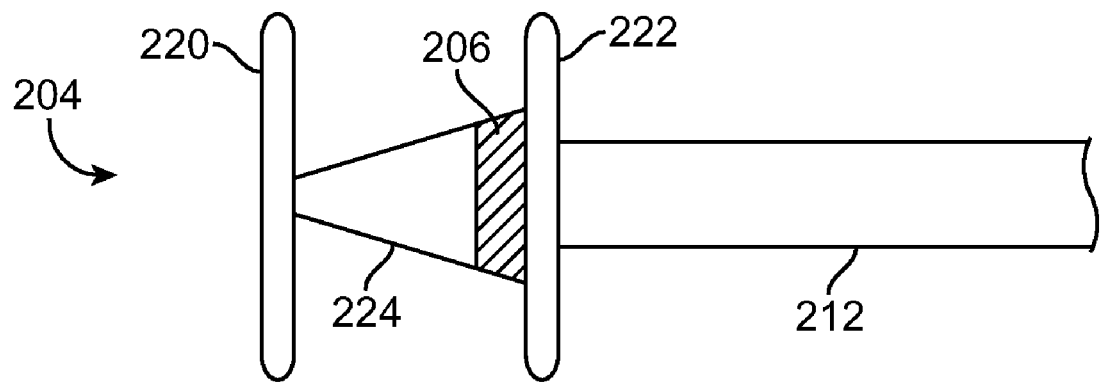
FIG. 12 illustrates an embodiment of a device having a conical segment.

It may be appreciated that the segment 224 may have a variety of shapes, sizes and lengths. For example, FIG. 12 illustrates an embodiment having a conical segment 225. In some embodiments, a nominal angle of the conical segment 225 is in the range of approximately 2 degrees to 10 degrees, preferably approximately 5 degrees. The conical shape may assist in securing the distal end 216 of the lead 204 to the stomach wall W. During digestion, the stomach produces slow contractile waves that propagate from the fundus toward the pylorus. During digestion, the average frequency of gastric slow waves in the stomach is approximately three times per minute. Upon each contractile wave reaching the lead 204 implant site, the muscularis layer MS of the stomach will constrict and contract circumferentially around the conical segment 225, while also increasing in thickness. Because of the conical shape of the segment 225, the circumferential constriction force acting on the surfaces of the conical segment 225 will be converted to a force vector which acts along the longitudinal axis of the conical segment 225 to push the fixation feature 222 against the stomach wall W, thus seating the fixation feature 222 onto the outer surface OS of the stomach wall W. Such seating assists in securing the fixation feature 222 to the stomach wall W during the healing process. Once the healing response has stabilized, the distal end 216 of the lead 204 will be desirably positioned to provide stable and repeatable electrical stimulation to the stomach wall W.

The one or more electrodes 206 include at least one stimulation electrode and optionally at least one return electrode. The at least one stimulation electrode is positioned so as to stimulate at least a portion of the stomach wall W. Therefore, the at least one stimulation electrode is typically positioned along a surface of the distal end 216 of the lead 204 which is in close proximity to a layer of the stomach wall W or contacts a layer of the stomach wall W at the time of implantation and/or after the healing response. Such surfaces typically include surfaces of the retention feature 220, the segment 224 and/or the fixation feature 222. In one embodiment, one or more stimulation electrodes positioned along these surfaces stimulate the muscularis layer MS of the stomach wall W.

In some embodiments, one or more of the stimulation electrodes also acts as a return electrode. In other embodiments, the stimulator 202 housing acts as a return electrode. In still other embodiments, at least one separate return electrode is present. The at least one return electrode may be disposed at any electrode location as described above. For example, the at least one return electrode may be disposed along any of the surfaces of the retention feature 220, segment 224, and/or fixation feature 222. Alternatively or in addition, the at least one return electrode may be disposed along the lead body 212 at a location proximal to the fixation feature 222. It may be appreciated that any number and combination of stimulation and return electrodes may be present and at any location.

When the at least one return electrode is located along the lead body 212 proximal to the fixation feature 222, the at least one return electrode may be in contact with the omentum or other visceral organs immediately after implantation. However, as chronic healing occurs, the lead 204 typically becomes encased in a fibrous pocket or capsule. The fibrous capsule surrounding the at least one return electrode may serve as a virtual electrode itself that provides a conductive interface between the at least one return electrode and the path to the at least one stimulation electrode. As the fibrosed pocket forms, the position of the at least one return electrode may change slightly from its original implant location, but with little consequence.

As the fibrous encapsulation surrounds the retention feature 220 and extends through the serosal layer SR, the fibrous encapsulation tissue creates a molded pocket within the stomach wall having the shape of the distal end 216 of the lead 204. This in turn further secures the lead 204 in place. The fibrous tissue itself may function as a virtual electrode to conduct energy to the at least one return electrode. Therefore, stimulation current vectors between the at least one stimulation electrode and the at least one return electrode can be described for both the acute (initial implant) and chronic (after fibrous encapsulation) stages. Acutely, stimulation current supplied by the stimulator 202 will flow along vectors between the stimulation electrode(s) in direct contact with the stomach wall W and the at least one return electrode in contact with the visceral organs or the omentum. Chronically, stimulation current supplied by the stimulator 202 will flow along vectors between the stimulation electrode(s) now contained within the fibrous pocket and the at least one return electrode which is now also contained within the fibrous pocket but positioned external to and beyond the serosal layer SR.

In a particular embodiment, a stimulation electrode is positioned along a surface of the distal end 216 of the lead 204, in close proximity to a layer of the stomach wall W or in contact with a layer of the stomach wall W, and a return electrode is positioned along the lead body 212 proximal to the fixation feature 222. In this embodiment, the distance between the stimulation electrode and the return electrode is in the range of approximately 1 cm to 10 cm. Further, in this embodiment, the surface area of the return electrode may be significantly larger than that of the stimulation electrode. An example ratio for the relative conductive surface areas of the return electrode to the stimulation electrode is 10:1, however other ratios may be used. The ratio of the relative conductive surface areas may be adjusted such that the current density delivered to tissue surrounding the stimulation electrode is sufficient to illicit the desired clinical symptoms, yet the current density associated with tissue surrounding the return electrode is distributed and lowered to be below a threshold to stimulate or otherwise impart a significant effect on the surrounding tissue. This configuration is referred to as unipolar stimulation. In some embodiments, the surface area of the stimulation electrode is in the range of approximately 0.5 square millimeters to 5 square millimeters, but is not so limited.

Referring back to FIG. 7, after the fixation feature 222 is attached to the serosal layer SR, the guide wire 100 is removed, leaving the lead 204 in place. The guide wire 100 may be removed through the mouth or through the abdomen. Removal through the mouth avoids any potential transfer of stomach contents to the peritoneal cavity. Such removal through the mouth is typically achieved through a lumen in an endoscope or other device.

Once the guide wire 100 is removed, the opening in the mucosal layer MC left by the guide wire 100 may be closed via conventional methods. Typically, this is achieved by endoclipping. In this procedure, a small clip with articulating jaws is mounted at the distal end of a deployment catheter. Actuation of a proximal handle of the catheter moves the articulating jaws. The articulating jaws are opened and positioned across the opening in the mucosal layer MC, typically with the use of endoscopic visual guidance. Once the jaws engage the mucosal layer MC, the jaws are closed thereby pinching tissue over the opening. The jaws are then locked in place by manipulation of the proximal handle, and the clip is released from the deployment catheter. The deployment catheter is then retracted from the stomach. The location and orientation of clipping may be adjusted as needed to achieve an acute closure of the mucosal channel. The mucosal layer MC heals quickly, and within a few days the site will be healed, preventing efflux of gastric fluid from the stomach into the peritoneal cavity.

Figure 13:
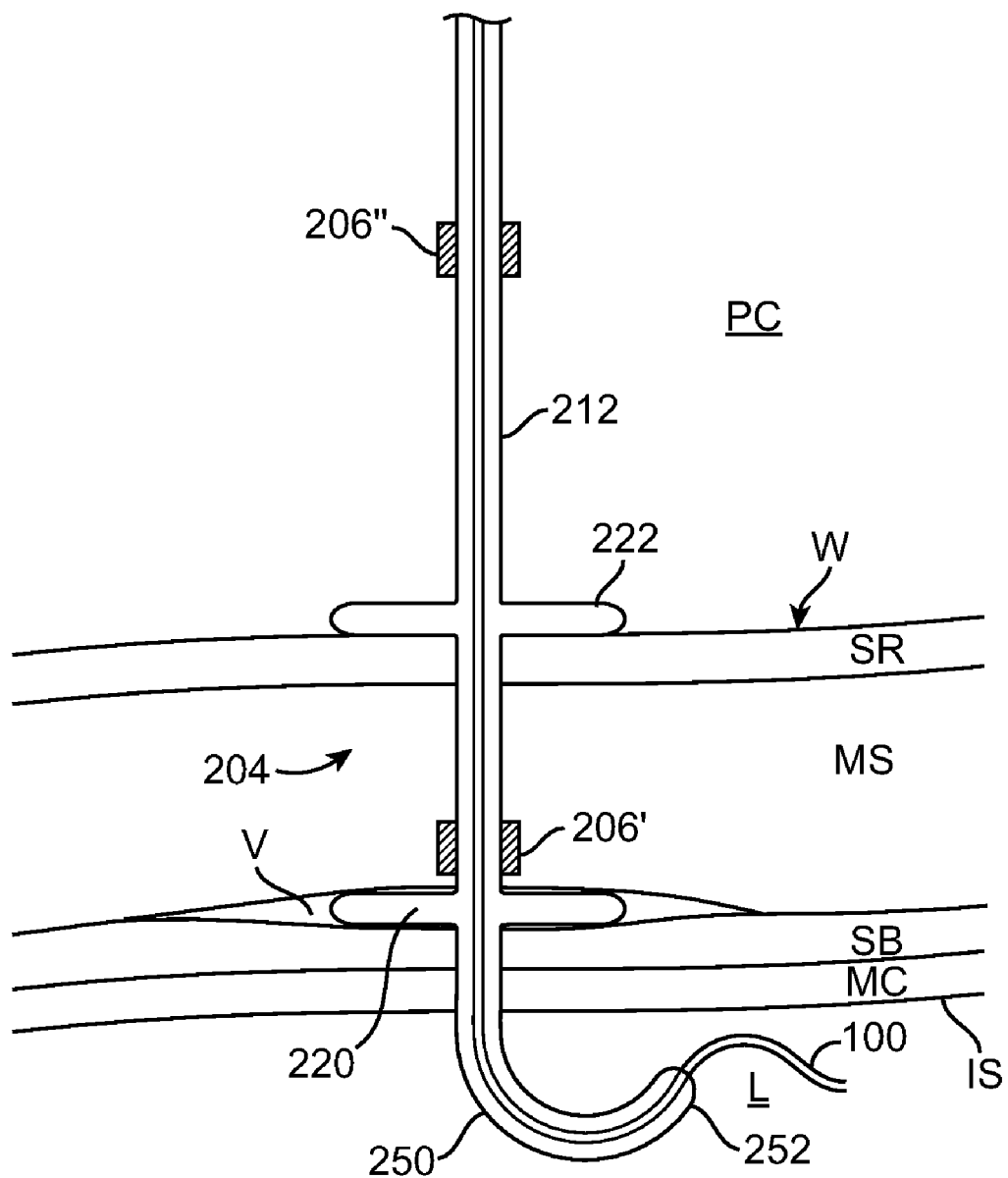
FIG. 13 illustrates an embodiment of a device having a distal segment which extends distally from the fixation retention feature.

Referring to FIG. 13, another embodiment of a lead 204 is illustrated. This embodiment is similar to the embodiment of FIG. 7, with the addition of a distal segment 250 which extends distally from the fixation retention feature 220. FIG. 13 shows the lead 204 advanced over a transectionally placed guide wire 100 which has been placed such as by an open, laparoscopic or modified percutaneous approach. In this embodiment, the lead 204 is advanced from outside the patient's abdomen, through the peritoneal cavity PC to the stomach wall W. The stomach wall W includes a serosal layer SR, a muscle layer MS, a submucosal layer SB, and a mucosal layer MC. The retention feature 220 is shown positioned between the muscle layer MS and the submucosal layer SB. Alternatively, the retention feature 220 may be positioned against the inner surface IS of the stomach wall W or between or within any layers of the stomach wall W. The distal segment 250 extends into the stomach lumen L. The distal segment 250 may include a variety of functional elements, such as at least one return electrode, a pH sensor, a piezoelectric film sensor, and/or a temperature sensor, to name a few. In addition, the guide wire 100 may extend through an opening in the tip 252, as shown, or through a sidewall of the distal segment 250.

The distal segment 250 may have any shape, length, curvature, dimension or size, to name a few. A nominal length of the distal segment 250 is approximately 10 mm. In this example, the tip 252 of the distal segment 250 curves toward the inner surface IS of the stomach wall W. In some embodiments, the distal segment 250 is curved so that the tip 252 contacts the mucosal layer MC and/or embeds within the mucosal layer MC or other layers of the stomach wall W. In these embodiments, the distal segment 250 may include a stimulation electrode wherein the stimulation electrode contacts one or more layers of the stomach wall W. Alternatively, the distal segment 250 may include a return electrode.

The lead 204 of FIG. 13 may be delivered to an implant site in a manner similar to the lead of FIG. 7. However, once the guide wire 100 has been removed, the opening in the mucosal layer MC is maintained by the distal segment 250. The features on the distal end of the lead prevent efflux of gastric fluid from the stomach into the peritoneal cavity.

Once one or more leads 204, of any of the embodiments described above, are implanted within the stomach wall W, the lead(s) are attached to the stimulator 202 and the stimulator 202 is implanted at an implant site within the patient. The implant site may be near or against the outer surface OS of the stomach, such as near the fixation feature 222 affixed to the serosal layer SR. Typically, the stimulator 202 is positioned within a subcutaneous pocket and affixed to muscular fascia with the use of suture, staple, darts, rivets or other mechanisms. Optionally, the lead body 212 may be coiled around or underneath the stimulator 202 to neatly package the system within the subcutaneous pocket. The pocket is then closed and the subcutaneously pathway and trans-dermal channel are closed by accepted surgical techniques.

Figure 14:
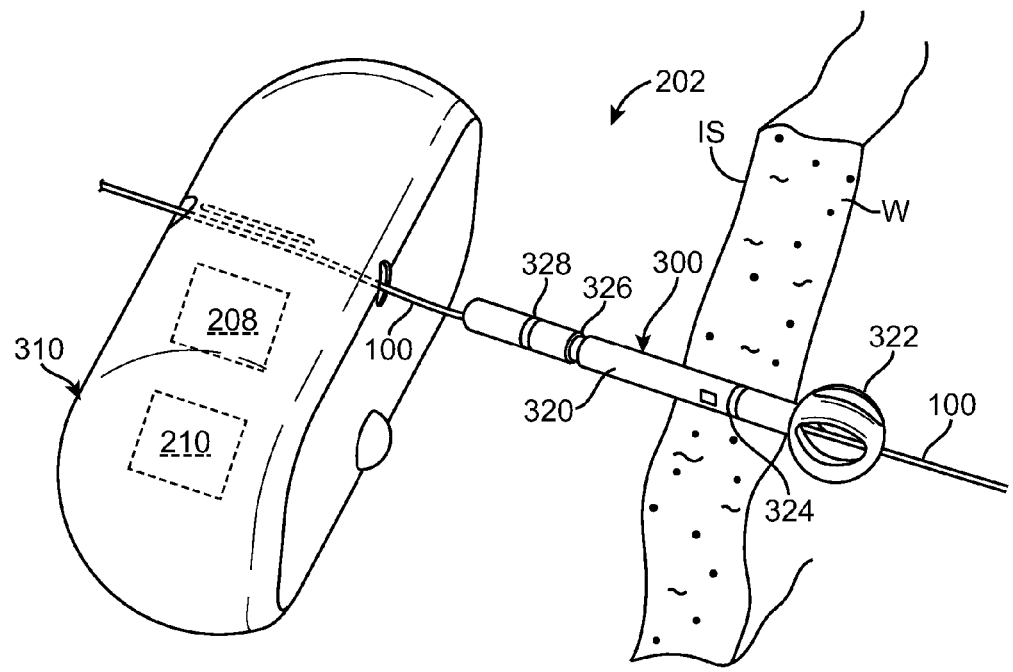
FIG. 14 illustrates another embodiment of a device which may be delivered by means of a transectionally place guide wire.

A variety of other devices and systems are also provided that may be delivered by means of a transectionally placed guide wire. For example, FIG. 14 illustrates a stimulator 202 which is attachable to the stomach wall W. The stimulator 202 is advanceable over a guide wire 100 which has been transectionally placed through the stomach wall W by an endoscopic, open, laparoscopic or modified percutaneous approach, as described above. The stimulator 202 comprises an anchor 300 and a main body portion 310. The anchor 300 comprises an elongate member 320 having an expandable distal end 322 and a stimulating electrode 324 in the form of a ring of a corrosion resistant metal conductor such as Platinum, Gold, Tantalum, Titanium or suitable alloys thereof, extending around the elongate member 320 just proximal of the expandable end 322. The main body portion 310 has electronics 208 and a power source 210 which provide electrical energy to the stimulating electrode 324. A notch 326 extending around the elongate member 320 is located proximally of the stimulating electrode 324, for connecting the anchor 300 to the main body portion 310. An electrical contact member 328 comprising a corrosion resistant metal ring extends circumferentially around the elongate member 320 proximal of the notch 326.

The electrode 324 and the contact 328 are electrically coupled through a wire or other conductor extending through the elongate member 320. The stimulator 202 of FIG. 14 is similar to the stimulators and devices provided in U.S. Pat. No. 6,535,764, incorporated herein by reference for all purposes, and therefore has many similar features and functions.

When the guide wire 100 is positioned to extend from the abdomen, through the stomach wall and through the mouth, such as illustrated in FIG. 5B, portions of the stimulator 202 may be delivered to the stomach wall W by different approaches. For example, the anchor 300 may be delivered to the stomach wall W through the abdomen and the main body portion 310 may be delivered to the inner surface IS of the stomach wall W through the mouth. The anchor 300 and main body portion 310 may then be joined. This may allow additional variations in design, such as a larger expandable end 322 which does not pass through the stomach wall W during delivery.

Figure 15:
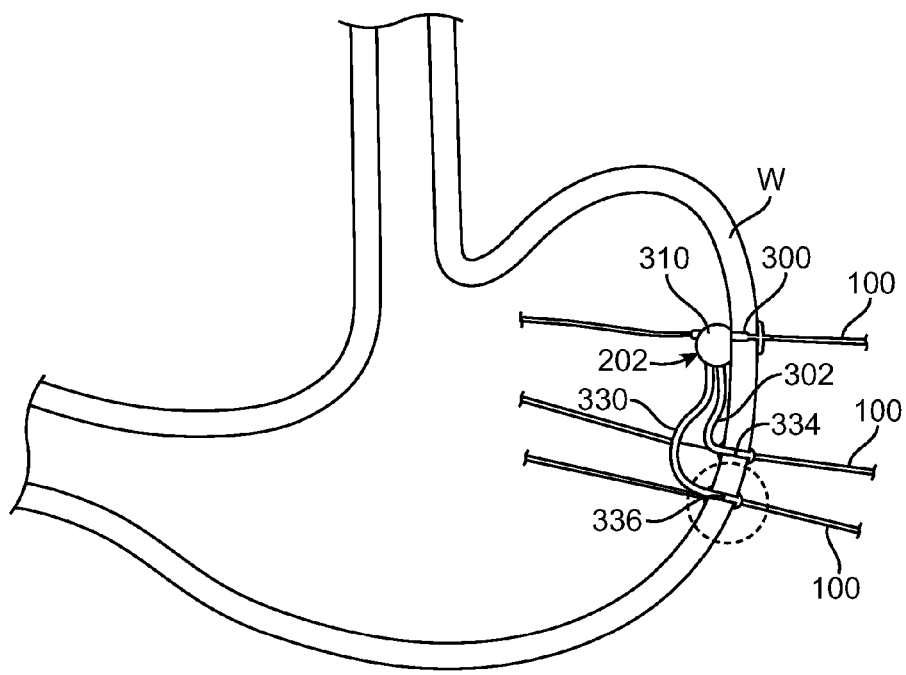
FIGS. 15, 16, 17 illustrates examples of systems which are attachable to the stomach wall with the use of one or more transectionally placed guide wires.

FIG. 15 illustrates an example of a system which is attachable to the stomach wall W with the use of one or more transectionally placed guide wires 100. Multiple guide wires may be placed, as shown, but more typically a single guide wire 100 will be placed at each implant location in a serial manner. The system comprises a stimulator 202 which is similar to the stimulator 202 described above in relation to FIG. 14 and to stimulators and devices provided in U.S. Pat. No. 6,535,764, incorporated herein by reference for all purposes. The stimulator 202 has a main body portion 310 and an anchor 300, each having a guide wire lumen therethrough or a tube thereattached which may be used in a similar manner. The stimulator 202 is coupled by leads 330, 332 to electrodes 334, 336. Each of the leads 330, 332 have a guide wire lumen through at least a portion or have a tube thereattached which may be used in a similar manner. The guide wire(s) 100 may be positioned with an endoscopic, open, laparoscopic or modified percutaneous approach, and optionally the guide wire(s) 100 may extend from the abdomen through to the mouth in some embodiments. The stimulator 202 and each of the electrodes 334, 336 are then delivered to the stomach wall W as desired. It may be appreciated that some of the elements may be attached to the stomach wall with the use of a transectionally place guide wire while other elements are attached by other methods.

Figure 16:
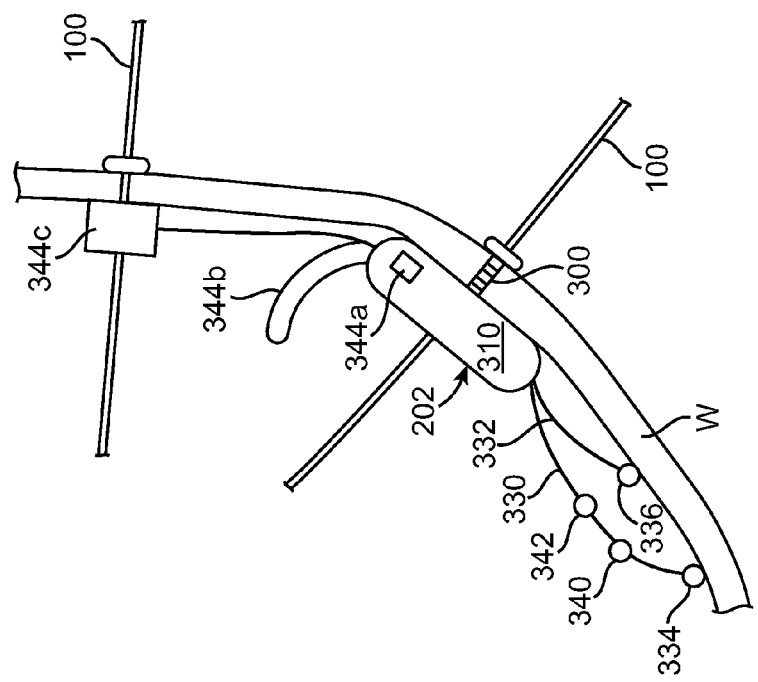

FIG. 16 illustrates another example of a system which is attachable to the stomach wall W with the use of one or more transectionally placed guide wires 100. Again, multiple guide wires may be placed, as shown, but more typically a single guide wire 100 will be placed at each implant location in a serial manner. The system comprises a stimulator 202 which is similar to stimulators and devices provided in U.S. patent application Ser. No. 10/950,345, filed Sep. 23, 2004, incorporated herein by reference for all purposes. The stimulator 202 comprises an anchor 300 and a main body portion 310, wherein the stimulator 202 is similar to the stimulator 202 described above in relation to FIG. 14 and to stimulators and devices provided in U.S. Pat. No. 6,535,764, incorporated herein by reference for all purposes. Each of the main body portion 310 and anchor 300 has a guide wire lumen therethrough or a tube thereattached which may be used in a similar manner. The stimulator 202 is coupled by leads 330, 332 to electrodes 334, 336, respectively. Each of the leads 330, 332 may have a guide wire lumen through at least a portion or have a tube thereattached which may be used in a similar manner. The guide wire(s) 100 may be positioned with an endoscopic, open, laparoscopic or modified percutaneous approach, and optionally the guide wire(s) 100 may extend from the abdomen through to the mouth in some embodiments. The stimulator 202 and each of the electrodes 334, 336 are then delivered to the stomach wall W as desired. It may be appreciated that some of the elements may be attached to the stomach wall with the use of a transectionally place guide wire while other elements are attached by other methods.

In the embodiment of FIG. 16, the system also includes separate impedance electrodes 340, 342 which are positioned to sense the impedance of contents of food in the stomach when they are interrogated. The impedance of the contents provides information on the food or liquid that has been ingested. Further, the system includes sensor 344a located on the main body portion 310 and a sensor 344b extending from the main body portion 310. Also, sensor 344c is located separately on the stomach wall W, also positionable by advancement over a transectionally placed guide wire 100 which is placed by an endoscopic approach, a laparoscopic approach or by a modified percutaneous approach. The sensors 344a, 344b, 344c may each comprise one or more sensors that provide feedback on a condition of a patient or information relating to the gastrointestinal system of the patient. The sensors 344a, 344b, 344c are positioned to directly sense information concerning the stomach and may include but are not limited to one or more of the following: temperature sensors, contraction sensors, pressure sensors, strain gauges, pH sensors, accelerometers, optical sensors.

Figure 17:
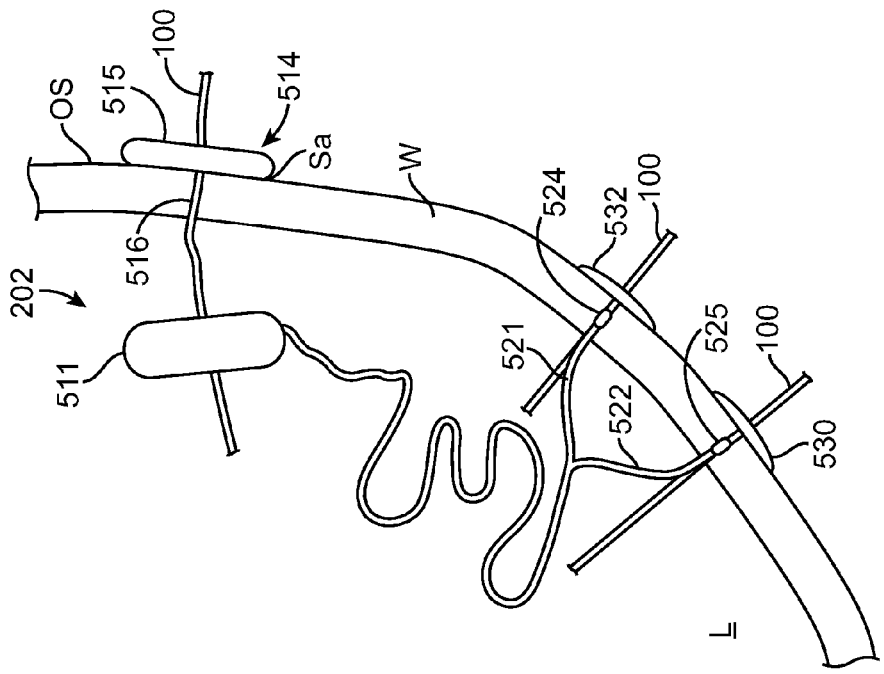

FIG. 17 illustrates another example of a system which is attachable to the stomach wall W with the use of one or more transectionally placed guide wires 100. The system is similar to systems and devices provided in U.S. patent application Ser. No. 10/992,382, filed Nov. 18, 2004, incorporated herein by reference for all purposes. The stimulator 202 comprises an anchor portion 514 and an electronics housing 511. The anchor portion 514 includes an expandable distal portion 515 and an elongate flexible portion 516 coupling the distal portion 515 to the housing 511. The expandable distal portion 515, elongate flexible portion 516, and optionally the housing 511 each have a guide wire lumen therethrough or a tube thereattached which may be used in a similar manner. The stimulator 202 is coupled by leads 521, 522 to electrodes 524, 525, respectively. Each of the leads 521, 522 may have a guide wire lumen through at least a portion or have a tube thereattached which may be used in a similar manner. Each of the guide wire(s) 100 may be positioned with an endoscopic, open, laparoscopic or modified percutaneous approach, and optionally each of the guide wire(s) 100 may extend from the abdomen through to the mouth in some embodiments. The stimulator 202 and each of the electrodes 524, 525 are then delivered to the stomach wall W by advancement over the appropriate guide wire, either from the mouth, abdomen or both. For example, the expandable distal portion 515 may be advanced through the mouth and stomach wall W to the outer surface OS of the stomach wall W where it is unfolded inflated or otherwise expanded, e.g., as a spring, from a first configuration to a second configuration. The expandable distal portion 515 has a surface area SA that interfaces with the outer surface OS. Or the expandable distal portion 515 may be advanced through the abdomen or peritoneal cavity and joined with the housing 511 or elongate flexible portion 516. The electrodes 524, 525 may be similarly placed, the anchors 530, 532 being advanced over the guide wire through the stomach wall W from the stomach lumen L or advanced over the guide wire through the abdomen and connecting with the leads 521, 522. It may be appreciated that some of the elements may be attached to the stomach wall with the use of a transectionally place guide wire while other elements are attached by other methods.

Figure 18:
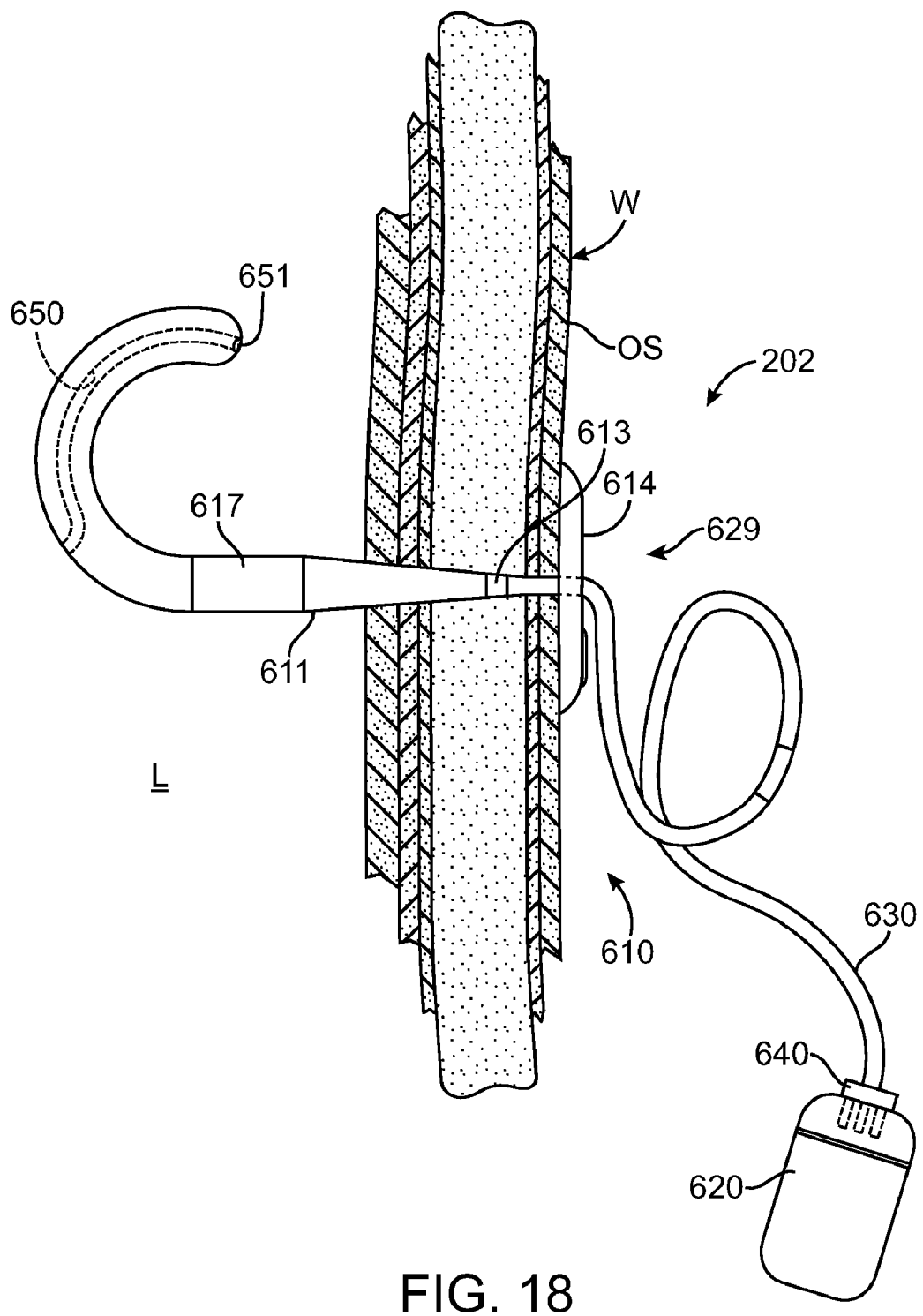
FIG. 18 illustrates another example of a system which is attachable to the stomach wall with the use of a transectionally placed guide wire.

FIG. 18 illustrates another example of a system which is attachable to the stomach wall W with the use of a transectionally placed guide wire. The system is similar to systems and devices provided in U.S. patent application Ser. No. 11/249,661, filed Oct. 12, 2005, incorporated herein by reference for all purposes. The stimulator 202 includes a lead 610 (shown implanted in a stomach wall W) coupled to stimulation electronic circuitry 620, (in this particular illustration, a subcutaneously implanted stimulator). The lead 610 comprises a retaining portion 629 including an elongate portion 611 coupled to an expandable anchor 614 where the expandable anchor 614 engages the outer surface OS of the stomach wall W and the elongate portion 611 extends through the stomach wall W and into the stomach lumen L. The lead 610 further comprises a lead wire 630 extending from the expandable anchor 614 to a connector 640 for connecting to the electronic circuitry 620 of the stimulator.

An electrode 613 is located on the expandable anchor 614 so that when the lead is implanted, the electrode 613 is located within the stomach wall W. A return electrode 617 is located on the elongate portion 611 within the stomach (alternatively within the stomach wall W). Return electrodes may be positioned in other locations. The expandable anchor 614 forms a plate that engages the outer surface OS of the stomach wall W to prevent the lead from advancing further into the stomach and to maintain the relative position of the electrode 613 within the stomach wall W. The plate can also be sutured to the outer surface OS.

The lead 610 also includes a guide wire opening 650 and through hole 651 for guiding the lead 610 over a transectionally placed guide wire during deployment. The guide wire would be placed through the stomach wall W at the location wherein the elongate portion 611 is shown passing through the wall W. The guide wire may be positioned with an open, laparoscopic or modified percutaneous approach, and optionally the guide wire may extend from the abdomen through to the mouth in some embodiments.

Figure 19A:
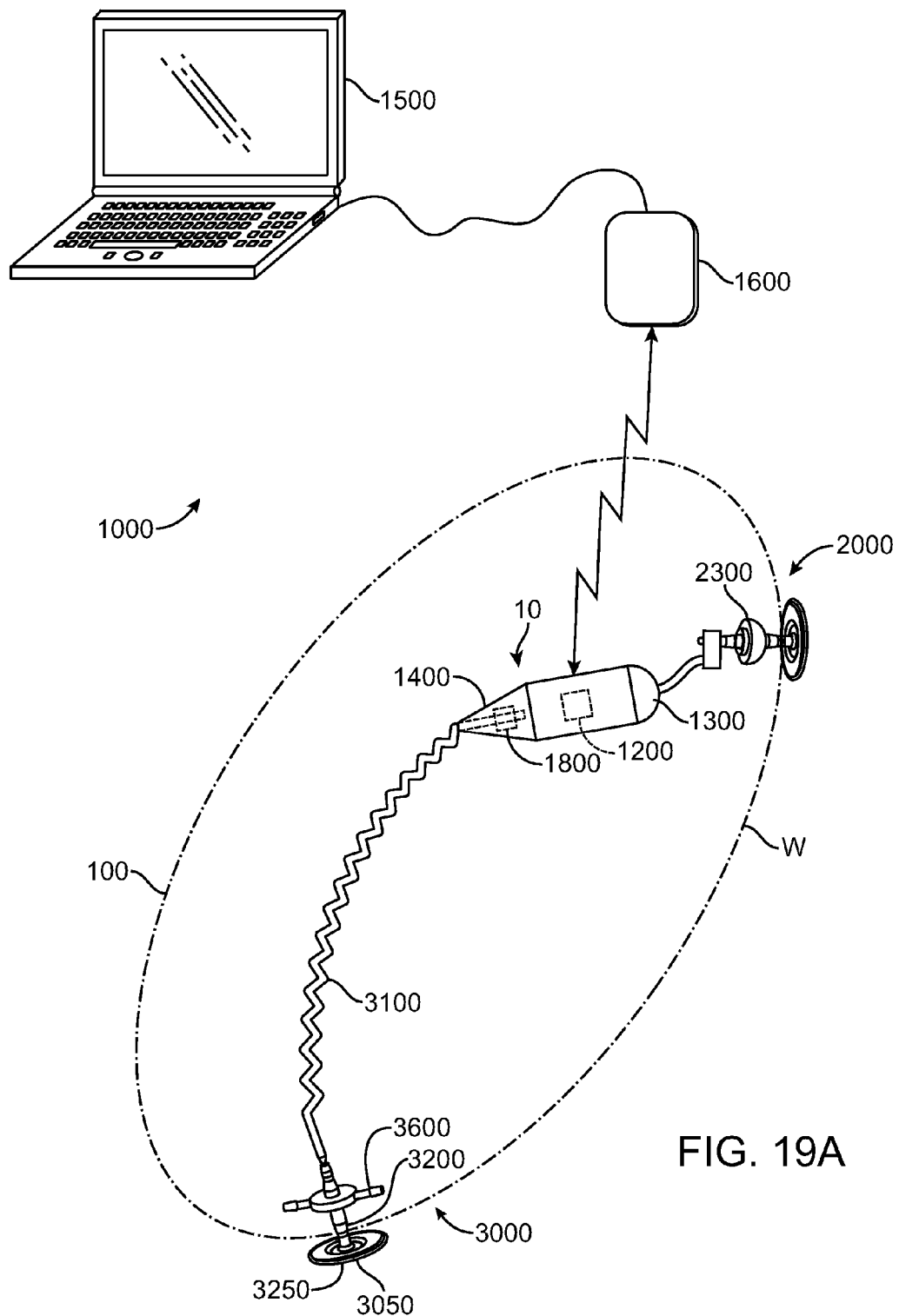
FIGS. 19A-19C illustrates a further example of a system which is attachable to the stomach wall with the use of a transectionally placed guide wire.
Figure 19B:
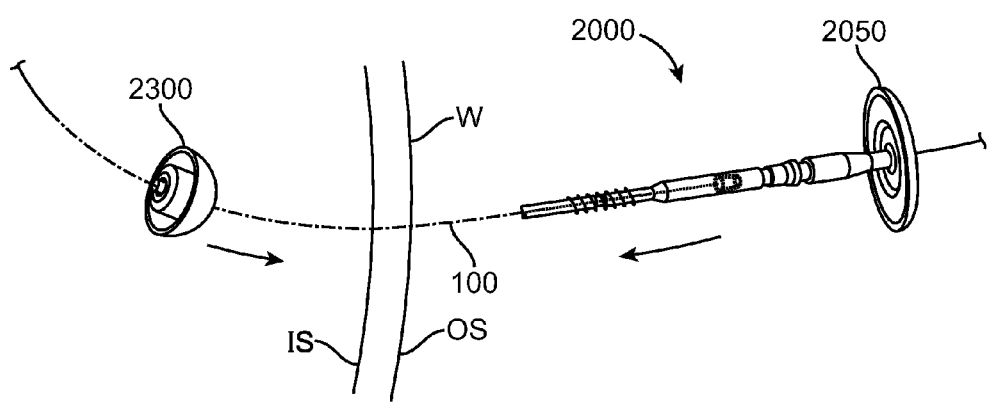

FIG. 19A illustrates another example of a system which is attachable to the stomach wall W with the use of a transectionally placed guide wire. The system is similar to systems and devices provided in U.S. Provisional Patent Application No. 60/815,640, filed Jun. 21, 2006, and U.S. patent application Ser. No. 11/766,660, filed Jun. 21, 2007, both incorporated herein by reference for all purposes. The stimulation system 1000 comprises a pulse generator or stimulator 10 which is implantable within an organ, such as a stomach 100, small intestine or colon. In this embodiment, the stimulator 10 comprises electronic circuitry 1200 contained within a protective housing 1300, an electronics anchor 2000, configured to anchor the electronics to the stomach wall W, and a lead anchor 3000, configured to anchor an electrode 3200 to the stomach wall W. Referring to FIG. 19B, the electronics anchor 2000 may be attached to the stomach wall W by advancement over a transectionally placed guide wire 100 through the stomach wall W. As shown, the electronics anchor 2000 is advanceable over the guide wire 100 from outside the stomach wall W. Thus, the anchor 2000 may be advanced from outside the body, through the abdomen, to the stomach wall W. A retaining element 2300 is advanceable over the guide wire 100 from inside the stomach wall. Thus, the retaining element 2300 may be advanced from outside the body, through the esophagus, to the stomach wall W. The anchor 2000 is advanced so that a portion extends through the wall W and a distal anchor portion 2050 resides adjacent to the outer surface OS of the wall W. The retaining element 2300 is then coupled or joined with the anchor 2000 so that the retaining element 2300 resides adjacent to the inner surface IS of the wall W.

Figure 19C:
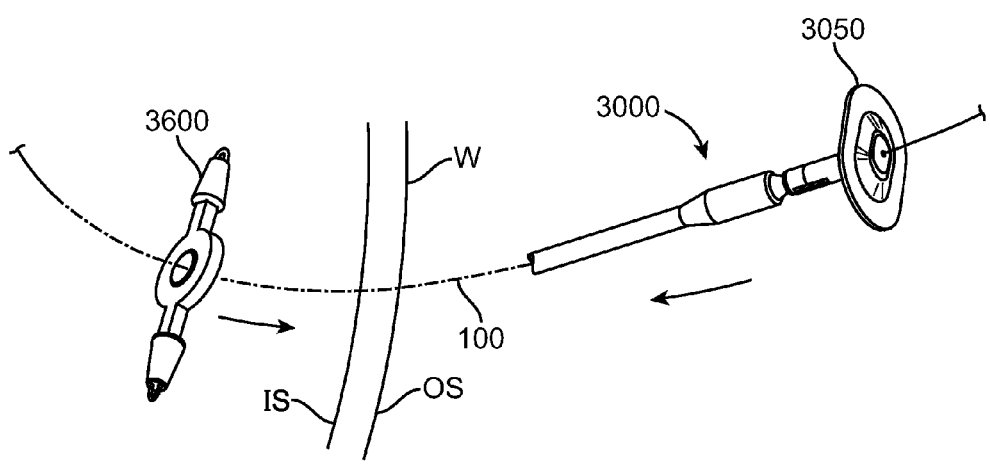

Similarly, referring to FIG. 19C, the lead anchor 3000 may be attached to the stomach wall W by advancement over a transectionally placed guide wire 100 through the stomach wall W. As shown, the lead anchor 3000 is advanceable over the guide wire 100 from outside the stomach wall W. Thus, the anchor 3000 may be advanced from outside the body, through the abdomen, to the stomach wall W. A retaining element 3600 is advanceable over the guide wire 100 from inside the stomach wall. Thus, the retaining element 3600 may be advanced from outside the body, through the esophagus, to the stomach wall W. The anchor 3000 is advanced so that a portion extends through the wall W and a distal anchor portion 3050 resides adjacent to the outer surface OS of the wall W. The retaining element 3600 is then coupled or joined with the anchor 3000 so that the retaining element 3600 resides adjacent to the inner surface IS of the wall W.

Figure 20:
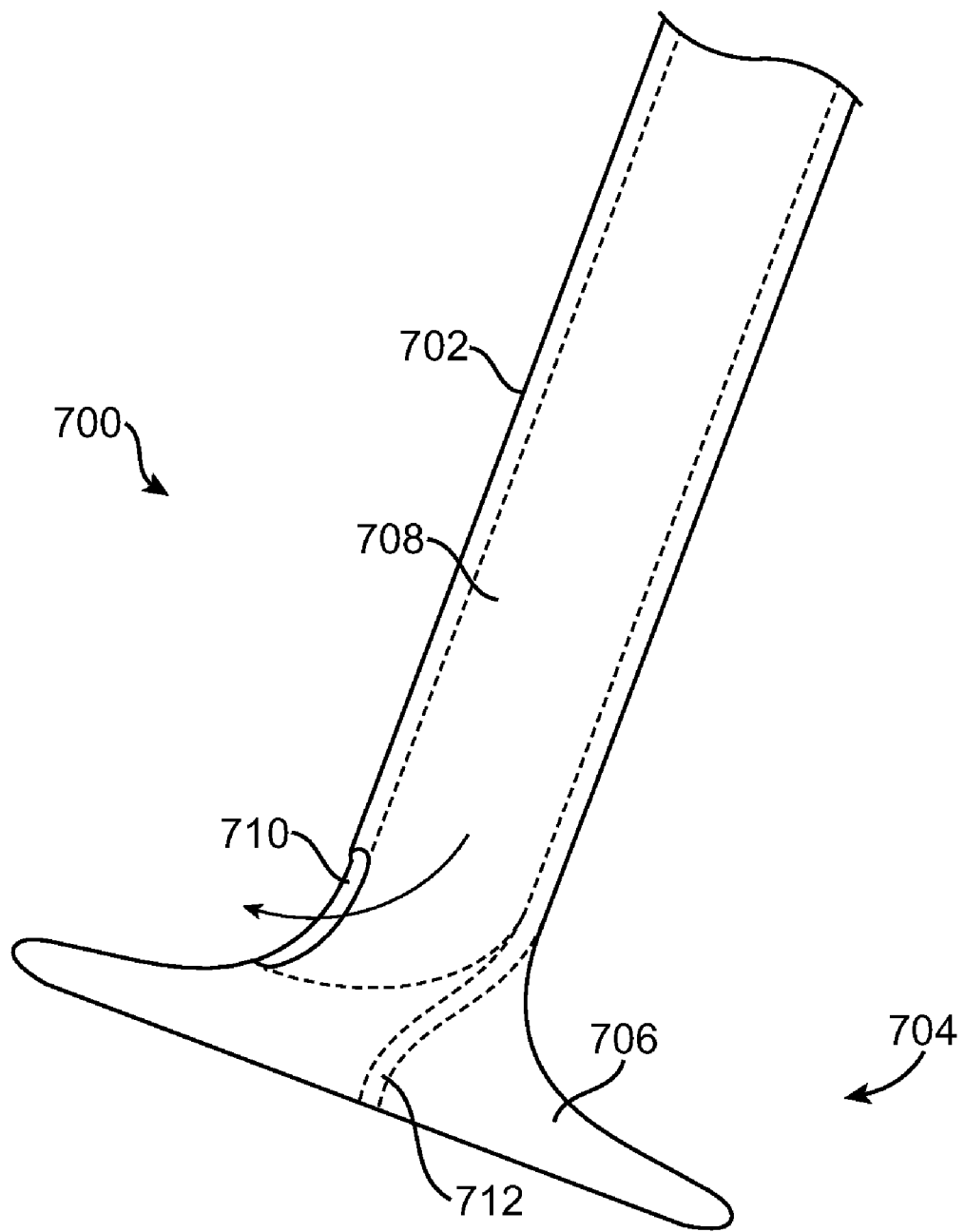
FIGS. 20, 21, 22 illustrate embodiments of delivery devices for use in delivering devices and systems in a direction substantially perpendicular to a transectionally placed guide wire.

In some embodiments, a transectionally placed guide wire is used to deliver devices and systems in a direction substantially perpendicular to the guide wire to locations within the stomach wall W, such as within the muscle layer MS or between various layers, such as between the muscle layer MS and the submucosal layer SB. To achieve this, a delivery device 700, such as illustrated in FIG. 20, may be used. In this embodiment, the delivery device 700 comprises an elongate shaft 702 having a distal end 704 and a radially protruding support 706 disposed near the distal end 704. In some embodiments, the radially protruding support 706 has a similar shape, dimension, material, form and/or functionality to the retention feature 220 described above, however other designs may be used. The delivery device 700 includes a delivery lumen 708 which extends through the shaft 702 to a port 710 located proximal to the protruding support 706. The delivery lumen 708 and port 710 are sized and shaped to allow passage therethrough of, for example, individual stimulation devices, such as the stimulation devices described in U.S. patent application Ser. No. 10/109,296, incorporated herein by reference for all purposes. In particular, one or more implantable stimulation devices sized and shaped to reside within the stomach wall W may be passed through the delivery lumen 708 and port 710. By positioning the radially protruding support 706 within or between the layers desired as the implant location, the radially protruding support 706 will guide the stimulation device to the desired implant location as the stimulation device is advanced through the port 710. The delivery device 700 also includes a guide wire lumen 712 for advancement over a guide wire.

Figure 21:
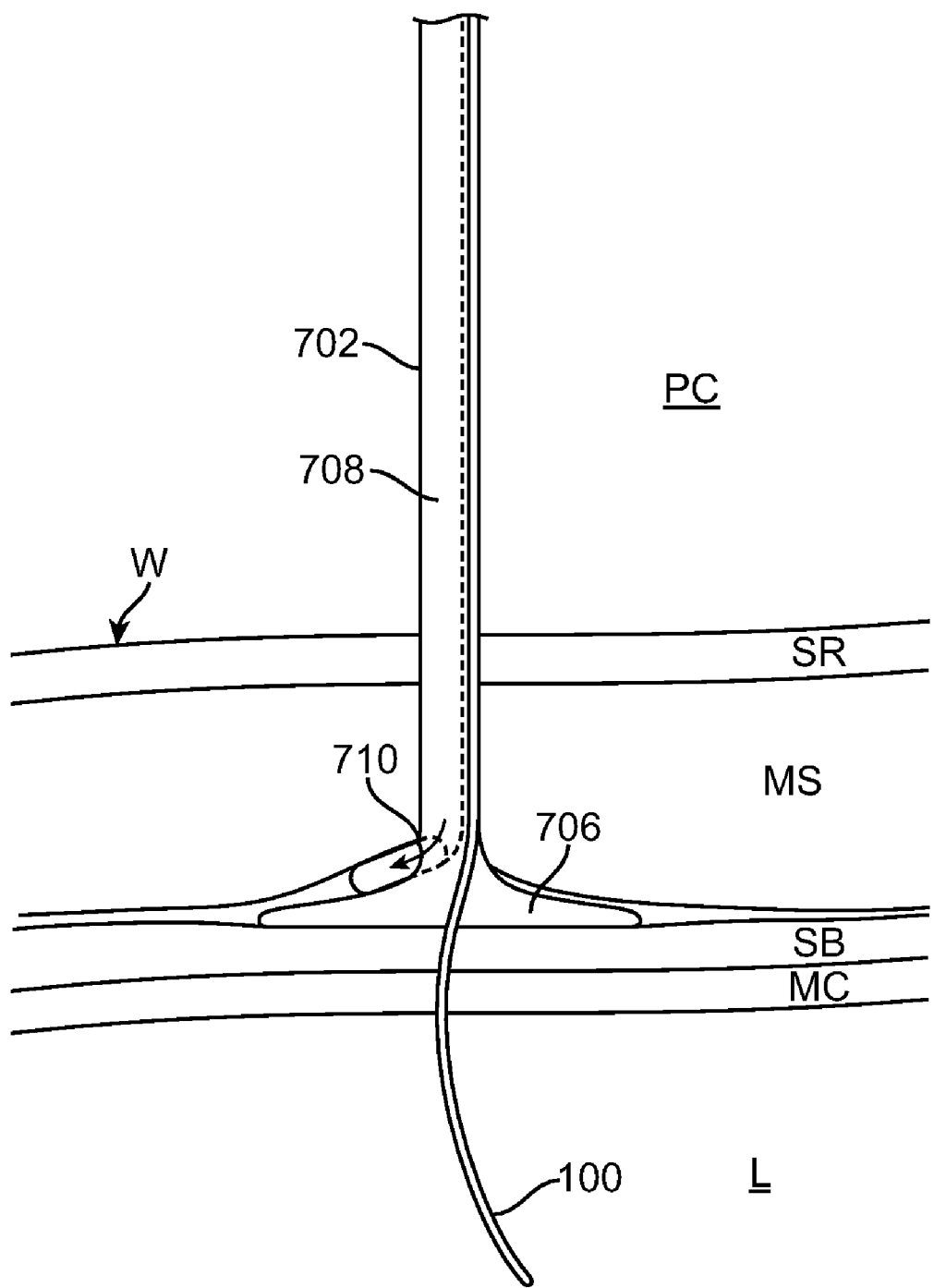

FIG. 21 illustrates the delivery device 700 advanced over a transectionally placed guide wire 100 (which has been positioned with an open, laparoscopic or modified percutaneous approach), wherein the radially protruding support 706 is positioned between the muscle layer MS and the submucosal layer SB in a manner similar to the placement of the retention feature 220 in FIG. 7. Thus, the delivery device 700 is advanced over the guide wire 100 through the peritoneal cavity PC to the stomach wall W. The radially protruding support 706 is positioned between the muscle layer MS and submucosal layer SB, as shown. A stimulation device 712 is then advanced through the delivery lumen 708 and the port 710 (such as with a plunger or pushrod) so that the support 706 guides the device 712 to a desired implantation site within the stomach wall W. It may be appreciated that in other embodiments the guide wire 100 may be placed by an endoscopic approach and the delivery device 700 advanced over the guide wire 100 through the stomach lumen L to the stomach wall W so that the radially protruding support 706 is positioned within or between the desired layers of the stomach wall W.

Figure 22:
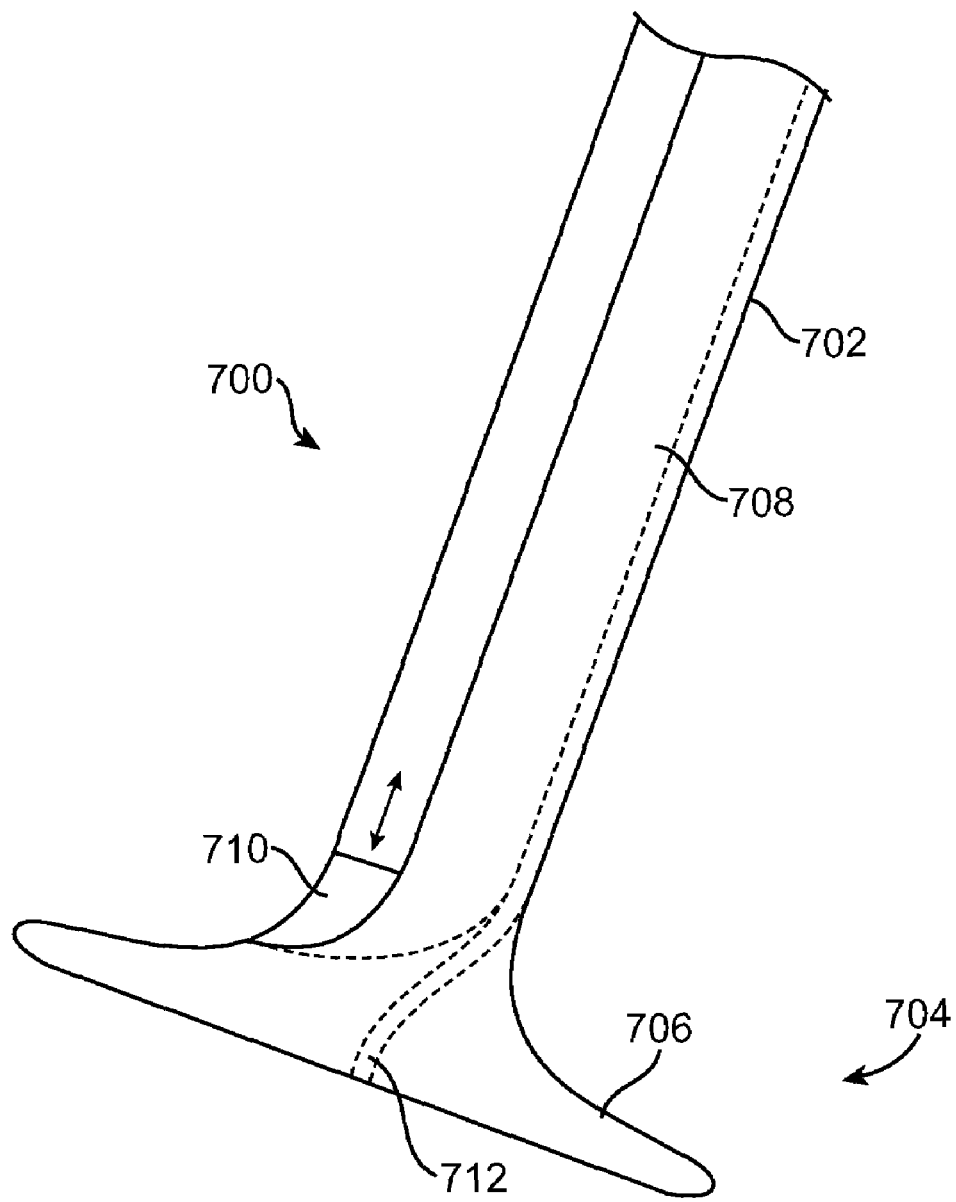

FIG. 22 illustrates another embodiment of a delivery device 700 comprising an elongate shaft 702 having a distal end 704 and a radially protruding support 706 disposed near the distal end 704. Again, the delivery device 700 includes a delivery lumen 708 which extends through the shaft 702 to a port 710 located proximal to the protruding support 706. In this embodiment, the size of the port 710 may be varied by movement of a sliding element 714. The sliding element 714 may be retracted to enlarge the port 710 or extended to reduce the port 710. Optionally, the sliding element 714 may be fully retracted and removed from the delivery device 700 so as to create an opening along the length of the delivery lumen 708. This may be useful when delivering stimulation devices or portions of stimulation devices that are implantable laterally within the stomach wall W but have at least a portion which extends through the wall to the stomach lumen L or peritoneal cavity PC. For example, a lead having an electrode may be advanced through the delivery lumen 708 so that the electrode passes through the port 710 to a desired implant location within the stomach wall W, the lead extending up through the delivery lumen 708. The sliding element 714 may then be retracted, releasing the lead from the delivery lumen 708. The delivery device 700 may then be removed leaving the lead in place, the electrode remaining implanted within the stomach wall W. Thus, the delivery device of FIG. 22 may be used to deliver a portions of stimulation devices, such as described in U.S. patent application Ser. No. 10/109,296 (particularly illustrated in FIGS. 9A, 10A), incorporated herein by reference for all purposes, and various leads such as described in U.S. Pat. Nos. 5,716,392; 5,836,994; 6,091,992, each of which are incorporated herein by reference for all purposes. It may also be appreciated that a guide wire may be advanced through the delivery lumen 708 which may then be used to deliver devices laterally within the stomach wall W, particularly after the delivery device has been removed.

It may be appreciated that the delivery devices of FIGS. 20, 21, 22 are merely examples and variations are included in the present invention. For example, the port 710 and/or radially protruding support 706 may be disposed at any locations along the shaft 702 and aligned with any desired tissue or anatomy. Thus, the radially protruding support 706 may be positioned against the inner surface IS of the stomach as the shaft 702 extends proximally into the peritoneal cavity PC. And, the port 710 may be spaced apart from the support 706 so it aligns with a desired layer of the stomach for implantation, such as the muscle layer MS. Advancement of a stimulation device or portion of a stimulation device through the port 710 directs the device to the desired layer. Alternatively, the radially protruding support 706 may be disposed proximal to the port 710 so that the support 706 is positioned against the outer surface OS of the stomach as the shaft 702 extends proximally into the peritoneal cavity PC. Again, the port 710 may be spaced apart from the support 706 so it aligns with a desired layer of the stomach for implantation, such as the muscle layer MS. Advancement of a stimulation device or portion of a stimulation device through the port 710 directs the device to the desired layer. Further, the delivery device may not include a radially protruding support 706 and the port 710 is simply aligned with the stomach wall W as desired.

Although the foregoing invention has been described in some detail by way of illustration and example, for purposes of clarity of understanding, it will be obvious that various alternatives, modifications and equivalents may be used and the above description should not be taken as limiting in scope of the invention which is defined by the appended claims.

What is claimed is:

1. A method of attaching a device having a first portion and a second portion to a wall of a hollow organ within a patient, the wall having an inner surface facing within the organ and an outer surface facing away from the organ, the method comprising:

positioning a guide wire wherein the guide wire transects the wall of the organ;

advancing the first portion of the device over the guide wire in a direction toward the inner surface of the wall of the hollow organ;

advancing the second portion of the device over the guide wire in an opposite direction toward the outer surface of the wall of the hollow organ; and joining the first and section portions together so as to attach the device to the wall of the hollow organ.

2. The method of claim 1, wherein positioning the guide wire comprises extending the guide wire through a mouth of the patient, and wherein advancing the first portion comprises advancing the first portion through the mouth and over the guide wire toward the inner surface of the wall of the hollow organ.

3. The method of claim 1, wherein positioning the guide wire comprises extending the guide wire through an abdomen of the patient, and wherein advancing the second portion comprises advancing the second portion through the abdomen and over the guide wire toward the outer surface of the wall of the hollow organ.

4. The method of claim 1, wherein positioning the guide wire comprises accessing the organ by a modified percutaneous approach without the use of general anesthesia, wherein the modified percutaneous approach comprises advancing a needle through an abdomen of the patient toward the outer surface of the organ, transecting the wall with the needle and advancing the guide wire through the needle.

5. The method of claim 4, wherein the modified percutaneous approach includes advancing a trocar through the abdomen of the patient toward the outer surface of the organ and advancing the needle through the trocar prior to transecting the wall with the needle.

* * * * *